US010016494B2

(12) United States Patent
Alfieri et al.

(10) Patent No.: US 10,016,494 B2
(45) Date of Patent: Jul. 10, 2018

(54) ANTIGENIC EPITOPES FROM EBV GP350/220 AND USES THEREOF

(71) Applicants: VALORISATION-HSJ, LIMITED PARTNERSHIP, Montreal (CA); VALORISATION-RECHERCHE, LIMITED PARTNERSHIP, Montreal (CA)

(72) Inventors: Caroline Alfieri, Dollard-des-Ormeaux (CA); Jerome Tanner, Dollard-des-Ormeaux (CA); Jing Hu, Montreal (CA); Jurgen Sygusch, Montreal (CA); Mathieu Coinçon, Stockholm (SE)

(73) Assignees: VALORISATION-HSJ, LIMITED PARTNERSHIP, Montreal (CA); VALORISATION-RECHERCHE, LIMITED PARTNERSHIP, Montreal (CA)

( * ) Notice: Subject to any disclaimer, the term of this patent is extended or adjusted under 35 U.S.C. 154(b) by 0 days.

(21) Appl. No.: 15/116,968

(22) PCT Filed: Feb. 6, 2015

(86) PCT No.: PCT/CA2015/050089
§ 371 (c)(1),
(2) Date: Aug. 5, 2016

(87) PCT Pub. No.: WO2015/117244
PCT Pub. Date: Aug. 13, 2015

(65) Prior Publication Data
US 2017/0189517 A1 Jul. 6, 2017

Related U.S. Application Data

(60) Provisional application No. 61/936,939, filed on Feb. 7, 2014.

(51) Int. Cl.

| | |
|---|---|
| *A61K 39/245* | (2006.01) |
| *C07K 14/05* | (2006.01) |
| *A61K 39/12* | (2006.01) |
| *G01N 33/68* | (2006.01) |
| *G01N 33/569* | (2006.01) |
| *C07K 16/08* | (2006.01) |

(52) U.S. Cl.
CPC ............ *A61K 39/12* (2013.01); *C07K 16/085* (2013.01); *G01N 33/56994* (2013.01); *G01N 33/6854* (2013.01); *C07K 2317/24* (2013.01); *C07K 2317/76* (2013.01); *C12N 2710/16222* (2013.01); *C12N 2710/16234* (2013.01); *G01N 2469/20* (2013.01)

(58) Field of Classification Search
None
See application file for complete search history.

(56) References Cited

FOREIGN PATENT DOCUMENTS

| | | | |
|---|---|---|---|
| WO | 99/02550 | A1 | 1/1999 |
| WO | 03/094962 | | 11/2003 |
| WO | 2013/143026 | A1 | 10/2012 |
| WO | 13/130565 | | 9/2013 |
| WO | 2014/018858 | A2 | 1/2014 |
| WO | PCT/CA2015/050089 | | 2/2015 |

OTHER PUBLICATIONS

Urquiza et al. Identification of Three gp350/220 Regions Involved in Epstein-Barr Virus Invasion of Host Cells. The Journal of Biological Chemistry Vol. 280, No. 42, pp. 35598-35605, Oct. 21, 2005.*
GenBank: AAA45881.1. Dated Aug. 2, 1993.*
Finerty et al., 1994. Immunization of cottontop tamarins and rabbits with a candidate vaccine against the Epstein-Barr virus based on the major viral envelope glycoprotein 318 gp340 and alum. Vaccine 12:1180-1184.

(Continued)

*Primary Examiner* — Nianxiang Zou
(74) *Attorney, Agent, or Firm* — Alain Dumont

(57) ABSTRACT

The present invention relates to a peptide comprising (A) (i) a first domain comprising an amino acid sequence having at least 60% sequence similarity with the sequence PDDRTLQ (SEQ ID NO:1); and (ii) a second domain covalently linked to the first domain and comprising an amino acid sequence having at least 60% sequence similarity with the sequence QNPVYLIPETVPYIKWDN (SEQ ID NO:2) or (B) (i) a first domain comprising an amino acid sequence having at least 60% sequence similarity with the sequence GSAK-PGNGSYF (SEQ ID NO: 41); and (ii) a second domain covalently linked to the first domain, said second domain comprising an amino acid sequence having at least 60% sequence similarity with the sequence SVKTEMLGNEID (SEQ ID NO: 42), wherein the peptide binds to monoclonal antibody clone 72A1. This peptide may be useful for inducing the production of neutralizing antibodies against a gp350-expressing herpesvirus, such as Epstein-Barr virus (EBV), for example for immunizing or vaccinating an animal against a gp350-expressing herpesvirus, as well as for detecting the presence or absence neutralizing anti-gp350-expressing herpesvirus antibodies in a sample.

16 Claims, 9 Drawing Sheets

(56) References Cited

OTHER PUBLICATIONS

Haque T. et al., 2006. A Mouse Monoclonal Antibody against Epstein-Barr Virus Envelope Glycoprotein 350 Prmievents Infection Both in Vitro and in vivo. The Journal of Infectious Diseases 194:584-7.
Hoffman et al., 1980. Monoclonal antibody against a 250,000-dalton glycoprotein of Epstein-Barr virus identifies a membrane antigen and a neutralizing antigen. Proc. Natl. Acad. Sci. U.S.A. 77:2979-2983.
Miller et al., 1982. Neutralization of lymphocyte immortalization by different strains of Epstein-Barr virus with a murine monoclonal antibody. Infect. Immun. 37:1028-1031.
Nemerow et al., 1989. Identification of an epitope in the major envelope protein of Epstein-Barr virus that mediates viral binding to the B lymphocyte EBV receptor (CR2). Cell 56:369-377.
Pither et al., 1992. Mapping of B-cell epitopes on the polypeptide chain of the Epstein-Barr virus major envelope glycoprotein and candidate vaccine molecule gp340. Journal of Virology 66(2):1246-1251.
Pither et al., 1992. Distribution of epitopes within the amino acid sequence of the Epstein-Barr virus major envelope glycoprotein, gp340, recognized by hyperimmune rabbit sera. Journal of General Virology 73:1409-1415.
Ogembo et al., 2013. Human complement receptor type 1/CD35 is an Epstein-Barr Virus receptor. Cell Rep. 3:371-385.
Qualtiere et al., 1987. Epitope mapping of the major Epstein-Barr virus outer envelope glycoprotein gp350/220. J. Gen. Virol. 68 (Pt 2):535-543.
Rees et al., 2009. A phase I trial of epstein-barr virus gp350 vaccine for children with chronic kidney disease awaiting transplantation. Transplantation 88:1025-1029.
Sircar et al., 2010. SnugDock: Paratope Structural Optimization during Antibody-Antigen Docking Compensates for Errors in Antibody Homology Models. PLoS. Compt. Biol. 6:e1000644.1-e1000644.13.
Sircar et al., 2009. Rosetta Antibody: Antibody variable region homology modeling. Nucleic Acids Res. 37:W474-W479.
Sitompul et al., 2012. Epitope mapping of gp350/220 conserved domain of epstein barr virus to develop nasopharyngeal carcinoma (npc) vaccine. Bioinformation 8(10):479-782.
Sokal et al., 2007. Recombinant gp350 vaccine for infectious mononucleosis: a phase 2, randomized, double-blind, placebo-controlled trial to evaluate the safety, immunogenicity, and efficacy of an Epstein-Barr virus vaccine in healthy young adults. J. Infect. Dis. 196:1749-1753.
Szakonyi et al., 2006. Structure of the Epstein-Barr virus major envelope glycoprotein. Nat. Stud. Mol. Biol. 13:996-1001.
Tanner et al., 1987. Epstein-Barr virus gp350/220 binding to the B lymphocyte C3d receptor mediates adsorption, capping, and endocytosis. Cell 50:203-213.
Tanner et al., 1988. Soluble gp350/220 and deletion mutant glycoproteins block Epstein-Barr virus adsorption to lymphocytes. J. Virol. 62:4452-4464.
Tanner et al., 1999. Epstein-Barr virus induces 403 Fas (CD95) in T cells and Fas ligand in B cells leading to T-cell apoptosis. Blood 94:3439-3447.
Tanner et al., 1996. Induction of interleukin-6 after stimulation of human B-cell CD21 by Epstein-Barr virus glycoproteins gp350 and gp220. J. Viral. 70:570-575.
Thorley-Lawson et al., 1980. Monoclonal antibodies against the major glycoprotein (gp350/220) of Epstein-Barr virus neutralize infectivity. Proc. Natl. Acad. Sci. U.S.A. 77:5307-5311.
Urquiza et al., 2005. Identification of three gp350/220 regions involved in Epstein-Barr virus invasion of host cells. J. Biol. Chem. 280:35598-35605.
Young et al., 2007. Isolating the Epstein-Barr virus gp350/220 binding site on complement receptor type 2 (CR2/CD21). The Journal of Biological Chemistry 282(50):36614-36625.
Young et al., 2008. Molecular basis of the interaction between complement receptor type 2 (CR2/CD21) and Epstein-Barr virus glycoprotein gp350. J. Virol. 82:11217-11227.
Zhang et al., 1991. Mapping of the epitopes of Epstein-Barr virus gp350 using monoclonal antibodies recombinant proteins expressed in *Escherichia coli* defines three antigenic determinants. Journal of General Virology 72:2747-2755.
Zhang et al., 1991 Conformation-dependent recognition of baculovirus-expressed Epstein-Barr virus gp350 by a panel of monoclonal antibodies. Journal of General Virology 74:2171-2179.
Uniparc accession No. UPI000108FEC0.
Supplementary Partial European Search Report and provisional Opinion in respect of EP 15 74 5772.
Supplementary European Search Report and Written Opinion in respect of EP 15 74 5772.

* cited by examiner

Mature chimeric light chain (SEQ ID NO: 5):

VLSQLVMTQSPKSMSMSVGERVTLTCKASENVVTYVSWYQQKPEQSPKLLIYGASNRYTGVP
DRFTGSGSATDFTLTISSVQAEDLADYHCGQGYSYPYT¦FGGGTKLEIKRADAAPTVSIFPPSSE
QLTSGGASVVCFLNNFYPKDINVKWKIDGSERQNGVLNSWTDQDSKDSTYSMSSTLTLTKDEY
ERHNSYTCEATHKTSTSPIVKSFNRNEC

Mature chimeric heavy chain (SEQ ID NO: 6):

DVQLVESGGGLVQPGGSRKLSCAASGFTFSSFGMHWVRQAPEKGLEWVAYISSGSSTLHYA
DTVKGRFTISRDNPKNTLFLQMTSLRSEDTAMYYCARWGNYPHYAMDY¦WGQGTMVTVSSAS
TKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTVL
HQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHN
HYTQKSLSLSPGK

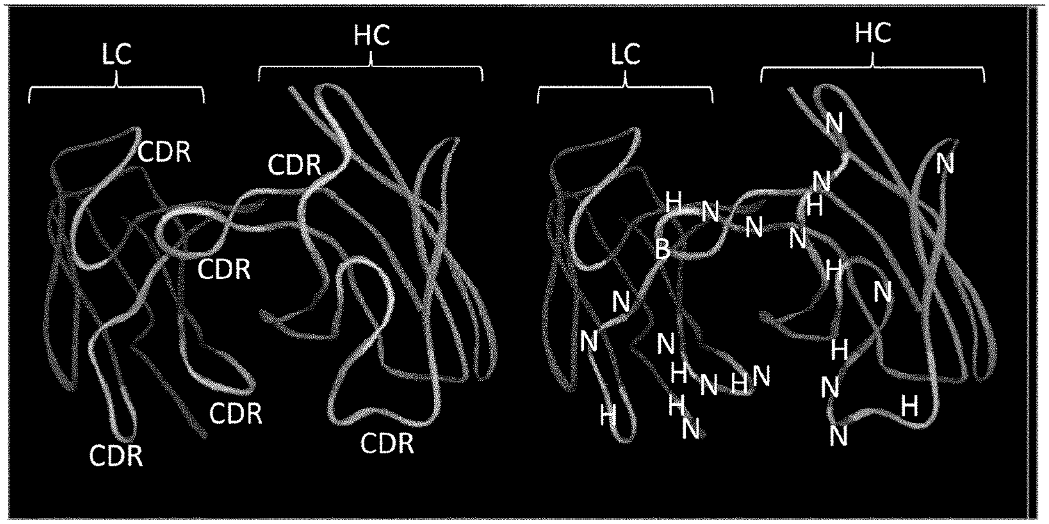

FIG. 1

ALLVCQYTIQSLI (1)QLTRDDPGFFNVEILEFPFYPACNVCTADVNATINFDVGGKKHKLNLDF
GLLTPHTKAVYQPRGAFGGSENATNLFLLELLGAGELALTMRSKKLPINITAGEEQQVSLESV
DVYFQDVFGTMWC HHAEM (2) QNPVYLIPETVPYIKWDNCNSTNITAVVRAQGLDVTLPLS
LPTSAQDSNF(3) SVKTEMLGNEI DIECIMEDGEISQVLPGDNKFNITCSGYESHVPSGGIL
TSTSPVATPIPGTGYAYSLRLTPRPVSRFLGNNSIL YVFYSGNGP(4) KASGGDYCIQSNIVFS

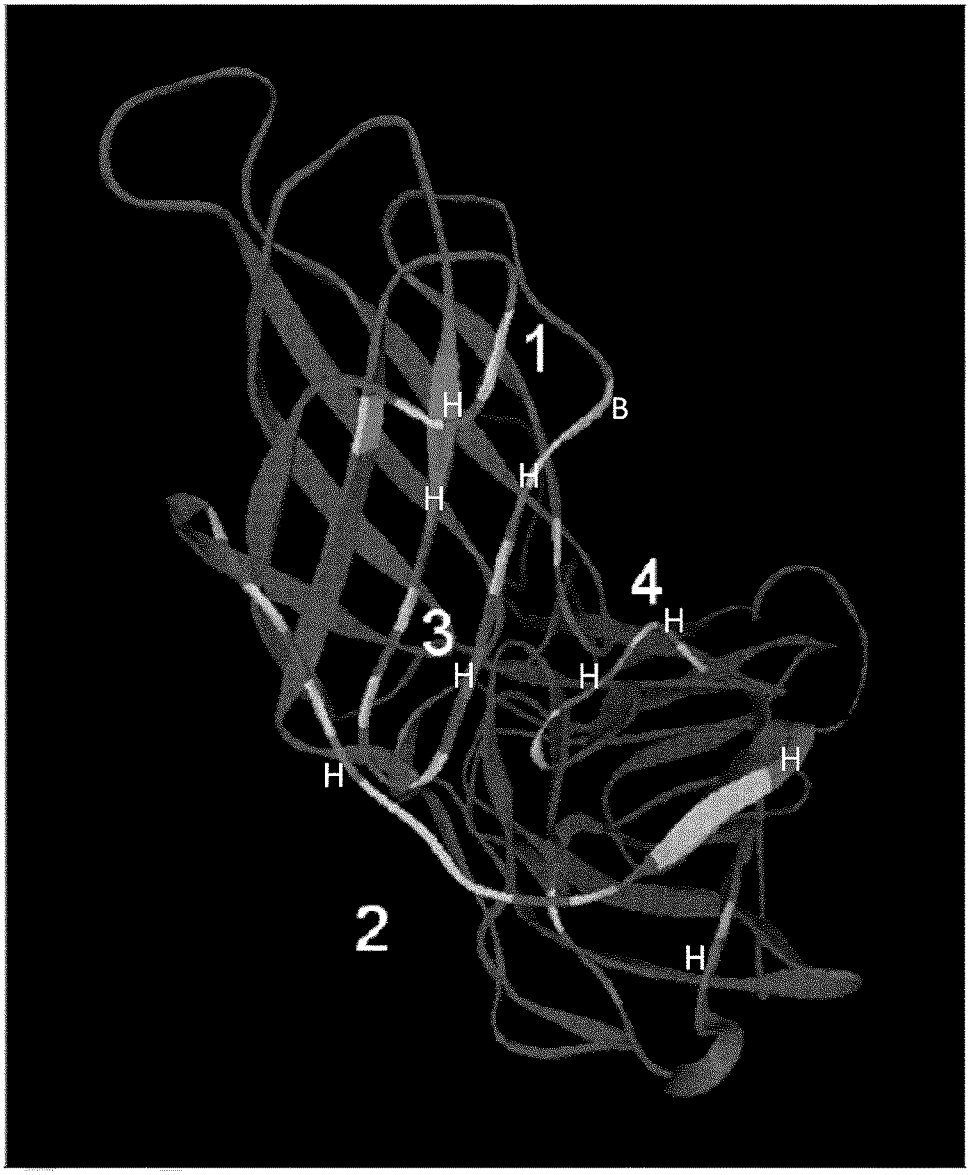

FIG. 3

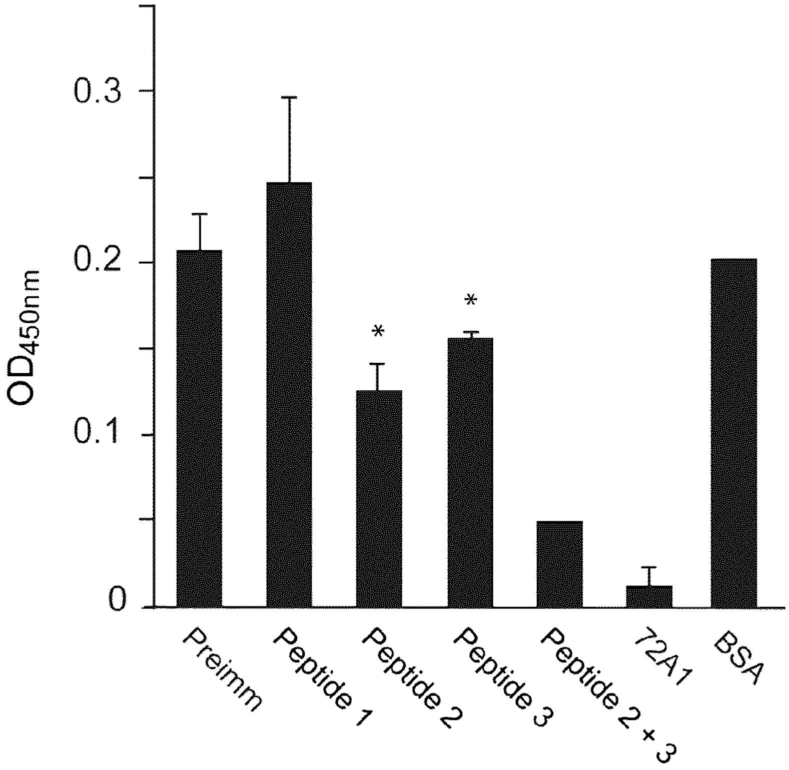

FIG. 7C

Gp350 (SEQ ID NO: 8)

MEAALLVCQYTIQSLIQLTRDDPGFFNVEILEFPFYPACNVCTADVNATINFDVGGKKHK
LNLDFGLLTPHTKAVYQPRGAFGGSENATNLFLLELLGAGELALTMRSKKLPINITTGEE
QQVSLESVDVYFQDVFGTMWCHHAEMQNPVYLIPETVPYIKWDNCNSTNITAVVRAQGLD
VTLPLSLPTSAQDSNFSVKTEMLGNEIDIECIMEDGEISQVLPGDNKFNITCSGYESHVP
SGGILTSTSPVATPIPGTGYAYSLRLTPRPVSRFLGNNSILYVFYSGNGPKASGGDYCIQ
SNIVFSDEIPASQDMPTNTTDITYVGDNATYSVPMVTSEDANSPNVTVTAFWAWPNNTET
DFKCKWTLTSGTPSGCENISGAFASNRTFDITVSGLGTAPKTLIITRTATNATTTTHKVI
FSKAPESTTTSPTLNTTGFAAPNTTTGLPSSTHVPTNLTAPASTGPTVSTADVTSPTPAG
TTSGASPVTPSPSPRDNGTESKAPDMTSPTSAVTTPTPNATSPTPAVTTPTPNATSPTLG
KTSPTSAVTTPTPNATSPTPAVTTPTPNATIPTLGKTSPTSAVTTPTPNATSPTVGETSP
QANTTNHTLGGTSSTPVVTSPPKNATSAVTTGQHNITSSSTSSMSLRPSSISETLSPSTS
DNSTSHMPLLTSAHPTGGENITQVTPASTSTHHVSTSSPAPRPGTTSQASGPGNSSTSTK
PGEVNVTKGTPPKNATSPQAPSGQKTAVPTVTSTGGKANSTTGGKHTTGHGARTSTEPTT
DYGGDSTTPRTRYNATTYLPPSTSSKLRPRWTFTSPPVTTAQATVPVPPTSQPRFSNLSM
LVLQWASLAVLTLLLLLVMADCAFRRNLSTSHTYTTPPYDDAETYV

FIG. 8A

Gp220 (SEQ ID NO: 9)

MEAALLVCQYTIQSLIQLTRDDPGFFNVEILEFPFYPACNVCTADVNATINFDVGGKKHK
LNLDFGLLTPHTKAVYQPRGAFGGSENATNLFLLELLGAGELALTMRSKKLPINITTGEE
QQVSLESVDVYFQDVFGTMWCHHAEMQNPVYLIPETVPYIKWDNCNSTNITAVVRAQGLD
VTLPLSLPTSAQDSNFSVKTEMLGNEIDIECIMEDGEISQVLPGDNKFNITCSGYESHVP
SGGILTSTSPVATPIPGTGYAYSLRLTPRPVSRFLGNNSILYVFYSGNGPKASGGDYCIQ
SNIVFSDEIPASQDMPTNTTDITYVGDNATYSVPMVTSEDANSPNVTVTAFWAWPNNTET
DFKCKWTLTSGTPSGCENISGAFASNRTFDITVSGLGTAPKTLIITRTATNATTTTHKVI
FSKAPESTTTSPTLNTTGFAAPNTTTGLPSSTHVPTNLTAPASTGPTVSTADVTSPTPAG
TTSGASPVTPSPSPRDNGTESTPPKNATSPQAPSGQKTAVPTVTSTGGKANSTTGGKHTT
GHGARTSTEPTTDYGGDSTTPRTRYNATTYLPPSTSSKLRPRWTFTSPPVTTAQATVPVP
PTSQPRFSNLSMLVLQWASLAVLTLLLLLVMADCAFRRNLSTSHTYTTPPYDDAETYV

FIG. 8B

ANTIGENIC EPITOPES FROM EBV GP350/220 AND USES THEREOF

CROSS REFERENCE TO RELATED APPLICATIONS

The present application is a National Entry Application of PCT application no PCT/CA2015/050089 filed on Feb. 6, 2015, and published in English under PCT Article 21(2), which itself claims the benefits of U.S. Provisional Application No. 61/936,939 filed Feb. 7, 2014. The content of all documents above is incorporated herein by reference in its entirety.

TECHNICAL FIELD

The present invention generally relates to Epstein-Barr virus (EBV) infection and more particularly to the neutralization of EBV using blocking antibodies.

SEQUENCE LISTING

Pursuant to 37 C.F.R. 1.821(c), a sequence listing is submitted herewith as an ASCII compliant text file named "12810_595-Seq Listing_ST25.txt", created on Aug. 3, 2016 and having a size of ~29 kilobytes. The content of the aforementioned file is hereby incorporated by reference in its entirety.

BACKGROUND ART

Epstein-Barr virus (EBV) is the etiologic agent of infectious mononucleosis (IM), a co-factor in nasopharyngeal carcinoma and certain forms of B, NK and T cell lymphomas, and the root cause of B-cell lymphoproliferative disease in individuals with weakened immune systems. Although ubiquitous worldwide, nearly 50% of young adults and children in developed countries are susceptible to primary EBV infection and debilitating IM. An important clinical consequence of primary EBV infection in immunosuppressed transplant patients is post-transplant lymphoproliferative disorder (PTLD). The relative hazard for PTLD is 4- to 6-fold higher in organ recipients who were EBV seronegative prior to transplant compared to organ recipients who were EBV seropositive.

The EBV major virion surface glycoprotein (gp)350 is the principal target of naturally-occurring neutralizing antibodies and is viewed as the best vaccine candidate to prevent IM in healthy EBV-naive young adults or to prevent PTLD in at-risk organ recipients. Antibodies reactive to a single epitope on the 350 kDa virion surface glycoprotein (gp)350 block virus infection in vitro and prevent B cell lymphoma in primates.

There is thus a need for a better understanding of the core peptide sequence recognized by the 72A1 monoclonal antibody to allow for the design of a peptide vaccine that focuses the humoral immune system to this epitope.

The present description refers to a number of documents, the content of which is herein incorporated by reference in their entirety.

SUMMARY OF THE INVENTION

The present invention provides the following items 1 to 29:

1. A peptide comprising:

(A)

(i) a first domain comprising an amino acid sequence having at least 60% sequence similarity with the sequence PDDRTLQ (SEQ ID NO: 1); and (ii) a second domain covalently linked to the first domain, said second domain comprising an amino acid sequence having at least 60% sequence similarity with the sequence QNPVYLIPETVPYIKWDN (SEQ ID NO: 2); or (B)

(i) a first domain comprising an amino acid sequence having at least 60% sequence similarity with the sequence GSAKPGNGSYF (SEQ ID NO: 41); and (ii) a second domain covalently linked to the first domain, said second domain comprising an amino acid sequence having at least 60% sequence similarity with the sequence SVKTEMLGNEID (SEQ ID NO: 29);

wherein said peptide binds to monoclonal antibody clone 72A1 and/or generates antibodies that compete with or interfere with the binding of monoclonal antibody clone 72A1 to EBV gp350.

2. The peptide of item 1, wherein said first domain comprises an amino acid sequence having at least 70% sequence similarity with the sequence PDDRTLQ (SEQ ID NO: 1) or GSAKPGNGSYF (SEQ ID NO: 41).

3. The peptide of item 1, wherein said first domain comprises, or consists of, the amino acid sequence PDDRTLQ (SEQ ID NO: 1), DDRTLQ (SEQ ID NO: 3) or GSAKPGNGSYF (SEQ ID NO: 41).

4. The peptide of any one of items 1 to 3, wherein said second domain comprises an amino acid sequence having at least 70% sequence similarity with the sequence QNPVYLIPETVPYIKWDN (SEQ ID NO: 2) or SVKTEMLGNEID (SEQ ID NO: 29).

5. The peptide of any one of items 1 to 3, wherein said second domain comprises an amino acid sequence having at least 80% sequence similarity with the sequence QNPVYLIPETVPYIKWDN (SEQ ID NO: 2) or SVKTEMLGNEID (SEQ ID NO: 29).

6. The peptide of any one of items 1 to 3, wherein said second domain comprises, or consists of, the amino acid sequence QNPVYLIPETVPYIKWDN (SEQ ID NO: 2) or SVKTEMLGNEID (SEQ ID NO: 29).

7. The peptide of any one of items 1 to 6, further comprising a linker between said first and second domains.

8. The peptide of item 7, wherein said linker is an amino acid linker of 1 to 10 amino acids.

9. The peptide of item 7, wherein said linker is an amino acid linker of 1 to 5 amino acids.

10. The peptide of item 7, wherein said linker is an amino acid linker of 1 or 2 amino acids.

11. The peptide of item 7, wherein said linker comprises one or more alanine and/or leucine residues.

12. The peptide of any one of items 1 to 11, wherein said peptide comprises, or consists of, the amino acid sequence DDRTLQLAQNPVYLIPETVPYIKWDN (SEQ ID NO: 4) or GSAKPGNGSYFASVKTEMLGNEID (SEQ ID NO: 27).

13. A pharmaceutical composition comprising the peptide of any one of items 1 to 12 and a pharmaceutically acceptable carrier or excipient.

14. The pharmaceutical composition of item 13, further comprising a vaccine adjuvant.

15. An isolated antibody or an antigen-binding fragment thereof that specifically recognize the peptide of any one of items 1 to 12, wherein said antibody is not antibody clone 72A1 or an antibody comprising the complement determining regions of antibody clone 72A1.

16. The isolated antibody of item 15, wherein said antibody is a monoclonal antibody.

17. A method of inducing the production of neutralizing antibodies against a gp350-expressing herpesvirus in an animal, said method comprising administering an effective amount of the peptide of any one of items 1 to 12, or the composition of item 13 or 14, to said animal.

18. A method of immunizing or vaccinating an animal against a gp350-expressing herpesvirus, said method comprising administering an effective amount of the peptide of any one of items 1 to 12, or the composition of item 13 or 14, to said animal.

19. The method of item 17 or 18, wherein said gp350-expressing herpesvirus is Epstein-Barr virus (EBV).

20. The method of any one of items 17 to 19, wherein said animal is a human.

21. Use of the peptide of any one of items 1 to 12, or the composition of item 13 or 14, for inducing the production of neutralizing antibodies against a gp350-expressing herpesvirus in an animal.

22. Use of the peptide of any one of items 1 to 12, or the composition of item 13 or 14, for the manufacture of a medicament for inducing the production of neutralizing antibodies against a gp350-expressing herpesvirus in an animal.

23. Use of the peptide of any one of items 1 to 12, or the composition of item 13 or 14, for immunizing or vaccinating an animal against a gp350-expressing herpesvirus.

24. Use of the peptide of any one of items 1 to 12, or the composition of item 13 or 14, for the manufacture of a medicament for immunizing or vaccinating an animal against a gp350-expressing herpesvirus.

25. The use of any one of items 21 to 24, wherein said gp350-expressing herpesvirus is Epstein-Barr virus (EBV).

26. A method for detecting the presence or absence neutralizing antibodies against a gp350-expressing herpesvirus in a sample, the method comprising contacting the sample with the peptide of any one of items 1 to 12, and detecting the presence or absence of neutralizing antibodies/peptide complexes.

27. The method of item 26, wherein said sample is a biological sample from a subject.

28. The method of item 26 or 27, wherein said subject is infected with a gp350-expressing herpesvirus, or has been vaccinated or immunized against a gp350-expressing herpesvirus.

29. The method of any one of items 26 to 28, wherein said gp350-expressing herpesvirus is Epstein-Barr virus (EBV).

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIG. 1 shows the 72A1 antibody light (SEQ ID NO: 5) and heavy (SEQ ID NO: 6) chain variable region sequences. Top panels, Anti-gp350 chimeric antibody amino acid sequence with predicted CDRs (bold) and heavy (=) and light chain (–) amino acids that interact strongly with gp350. Amino-terminal peptide sequences were determined by Edman sequencing. The murine variable region and human Ig constant region junction is shown (¦). The bottom panel shows a 3D-depiction of the anti-gp350 antibody light chain (LC) and heavy chain (HC) variable regions with CDR amino acids (CDR) and interface with gp350 neutralization epitope (N) by contributing H-bonding (H) or forming a salt bridge (B) with gp350.

FIG. 3 depicts the amino acids on the surface of gp350 predicted to couple with the 72A1 variable region (SEQ ID NO: 7). Top panel, interfacing amino acids (bold) that H-bond or form a salt bridge with the 72A1 heavy chain (=) or light chain (–) variable region. Bottom panel, 3D depiction of the gp350 amino terminus showing the four interfacing peptide sequences (1-4) and internal amino acids that contribute H-bonding (H) or form a salt bridge (B) with the 72A1 antibody.

FIG. 4A: $OD_{450\ nm}$ values, derived from duplicate samples and from three separate experiments, were plotted as average OD value+SE. FIG. 4B: Percent inhibition derived from duplicate samples and from three separate experiments, were plotted as average inhibition+SE. Corresponding t-test p-values for P2, P1,2 and P2,3 verses P1 were ≤0.04.

FIG. 7C shows that Gp350 peptides generate anti-gp350 antibodies that block 72A1 recognition of gp350. Histogram of biotinylated-72A1 binding to gp350 protein that was pre-exposed to mouse preimmune (preimm) serum, pooled serum from peptide immunized mice (1:50 dilution), or 1 μg/ml 72A1, or 0.5 mg/ml BSA. Average OD±SEM was derived from three separate experiments. P-values≤0.05 are indicated (*).

FIGS. 8A and 8B show the amino acid sequence of EBV gp350 (SEQ ID NO: 8) and gp220 (SEQ ID NO: 9), respectively (UniProt: P68343).

DISCLOSURE OF INVENTION

Figure 2A:
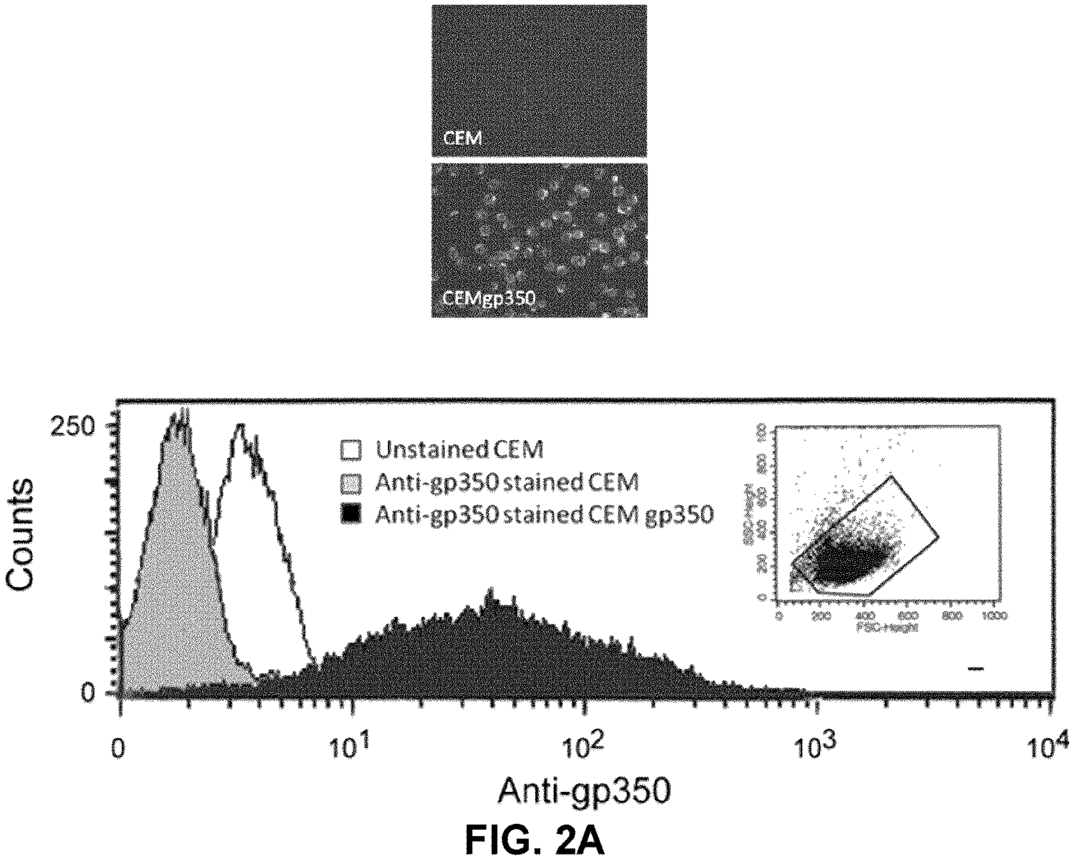
FIG. 2 shows that the chimeric anti-gp350 antibody recognizes native gp350 and blocks EBV infection of B cells. (A) Chimeric anti-g350 antibody recognized gp350 expressed on the surface of CEM cells (CEMgp350) as measured by immunofluorescence microscopy (left panel) or by flow cytometry analysis (right panel). (B) $Log_{10}$ doses of chimeric anti-gp350, or 72A1 antibody block P3HR1 virus superinfection of Raji cells.

Terms and symbols of genetics, molecular biology, biochemistry and nucleic acid used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like. All terms are to be understood with their typical meanings established in the relevant art.

The articles "a" and "an" are used herein to refer to one or to more than one (i.e. to at least one) of the grammatical object of the article. By way of example, "an element" means one element or more than one element. Throughout this specification, unless the context requires otherwise, the words "comprise," "comprises" and "comprising" will be understood to imply the inclusion of a stated step or element or group of steps or elements but not the exclusion of any other step or element or group of steps or elements.

The EBV major virion surface glycoprotein (gp)350 is the principal target of naturally-occurring neutralizing antibodies and is viewed as the best vaccine candidate to prevent IM in healthy EBV-naive young adults or to prevent PTLD in at-risk organ recipients (5,27). The 838 amino acid ectodomain of a mature 350 kDa molecule is highly glycosylated and, although it contains at least eight unique immunodominant B cell epitopes (25), experimental evidence indicates that only one epitope, represented by the neutralizing monoclonal antibody 72A1 (9), neutralizes infection by inhibiting EBV binding to the cellular receptors CD21 and CD35 (24,32). An electron density map of the first 440 amino acids of the gp350 molecule localize the virus neutralization epitope to a planar structure devoid of carbohydrates (31); however the amino acids within this gp350 surface structure that interact with the 72A1 antibody and constitute the strong EBV neutralization epitope are unknown.

In the studies described herein, the present inventors have provided insights into the gp350 neutralization domain and have developed synthetic gp350 mimetic peptides comprising the epitope recognized by the EBV neutralizing 72A1 antibody, i.e. the antibody produced by the murine 72A1 hybridoma cell line.

Accordingly, in a first aspect, the present invention provides a peptide comprising:

(A)

(i) a first domain comprising an amino acid sequence having at least 60% sequence similarity with the sequence PDDRTLQ (SEQ ID NO: 1); and (ii) a second domain covalently linked to the first domain, said second domain comprising an amino acid sequence having at least 60% sequence similarity with the sequence QNPVYLIPETVPYIKWDN (SEQ ID NO: 2); or (B)

(i) a first domain comprising an amino acid sequence having at least 60% sequence similarity with the sequence GSAKPGNGSYF (SEQ ID NO: 41); and (ii) a second domain covalently linked to the first domain, said second domain comprising an amino acid sequence having at least 60% sequence similarity with the sequence SVKTEMLGNEID (SEQ ID NO: 29);

wherein said peptide binds to monoclonal antibody clone 72A1 and/or generates antibodies that compete with or interfere with the binding of monoclonal antibody clone 72A1 to EBV gp350.

In another aspect, the present invention provides a peptide comprising:

(i) a first domain comprising an amino acid sequence having at least 60% sequence similarity with the sequence PDDRTLQ (SEQ ID NO: 1) or DDRTLQ (SEQ ID NO:3); and (i) a second domain covalently linked to the first domain, said second domain comprising an amino acid sequence having at least 60% sequence similarity with the sequence QNPVYLIPETVPYIKWDN (SEQ ID NO:2);

wherein said peptide binds to monoclonal antibody clone 72A1 and/or generates antibodies that compete with or interfere with the binding of monoclonal antibody clone 72A1 to EBV gp350. In an embodiment, said peptide binds to monoclonal antibody clone 72A1. In another embodiment, said peptide binds to monoclonal antibody clone 72A1 and generates antibodies that compete with or interfere with the binding of monoclonal antibody clone 72A1 to EBV gp350

In another aspect, the present invention provides a peptide comprising:

(i) a first domain comprising an amino acid sequence having at least 60% sequence similarity with the sequence GSAKPGNGSYF (SEQ ID NO: 41); and (ii) a second domain covalently linked to the first domain, said second domain comprising an amino acid sequence having at least 60% sequence similarity with the sequence SVKTEMLGNEID (SEQ ID NO: 29);

wherein said peptide binds to monoclonal antibody clone 72A1 and/or generates antibodies that compete with or interfere with the binding of monoclonal antibody clone 72A1 to EBV gp350. In an embodiment, said peptides generates antibodies that compete with or interfere with the binding of monoclonal antibody clone 72A1 to EBV gp350.

The expression "binds to monoclonal antibody clone 72A1" means that the peptide is able to bind to monoclonal antibody clone 72A1 with a detectable affinity, in an embodiment with an affinity constant ($K_D$) of at least 1 μM, in further embodiments with a $K_D$ of at least 0.1 μM, 0.01 μM, 1 nm or 0.1 nm. In an embodiment, the peptide competes for gp350 recognition by the 72A1 antibody. In another embodiment, the peptide binds to monoclonal antibody clone 72A1 with a higher affinity relative to a corresponding peptide comprising only the first domain or only the second domain defined above. Monoclonal antibody clone 72A1 is a well-known mouse monoclonal antibody (IgG1 isotype) that is commercially available (e.g., from EMD Millipore, catalog #MAB10219).

The expression "generates antibodies that compete with or interfere with the binding of monoclonal antibody clone 72A1 to EBV gp350" means that antibodies (purified or in a serum) generated in a suitable animal (mice, rabbits) using the peptide as an antigen/immunogen are capable of blocking (e.g., at least partially) the binding of monoclonal antibody clone 72A1 to the EBV protein gp350. This may be measured by ELISA, for example using the method described below.

The term "amino acid" as used herein includes both L- and D-isomers of the naturally occurring amino acids as well as other amino acids (e.g., naturally-occurring amino acids, non-naturally-occurring amino acids, amino acids which are not encoded by nucleic acid sequences, etc.) used in peptide chemistry to prepare synthetic analogs of peptides.

Examples of naturally-occurring amino acids are glycine, alanine, valine, leucine, isoleucine, serine, threonine, etc. Other amino acids include for example norleucine, norvaline, cyclohexyl alanine, biphenyl alanine, homophenyl alanine, naphthyl alanine, pyridyl alanine, phenyl alanine substituted at the ortho, para and meta positions with alkoxy, halogen or nitro groups etc. These amino acids are well known in the art of biochemistry/peptide chemistry. In an embodiment, the above-mentioned peptide comprises only L-amino acids.

"Similarity" or "identity" refers to sequence similarity between two polypeptide molecules. Similarity/identity can be determined by comparing each position in the aligned sequences. A degree of similarity/identity between amino acid sequences is a function of the number of identical amino acids at positions shared by the sequences. As the term is used herein, an amino acid sequence is "similar" to another sequence if the two sequences are substantially identical and the functional activity of the sequences is conserved. As used herein, a given percentage of similarity/identity between sequences denotes the degree of sequence identity in optimally aligned sequences.

Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerized implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215: 403-10 (using the published default settings). Software for performing BLAST analysis may be available through the National Center for Biotechnology Information web site (http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

In embodiments, the first domain comprises, or consists of, an amino acid sequence having at least 65, 70, 75, 80, 85, 90 or 95% sequence similarity with the sequence PDDRTLQ (SEQ ID NO:1), DDRTLQ (SEQ ID NO:3) or GSAKPGNGSYF (SEQ ID NO: 41).

In embodiments, the first domain comprises, or consists of, an amino acid sequence having at least 65, 70, 75, 80, 85, 90 or 95% sequence similarity with the sequence PDDRTLQ (SEQ ID NO:1) or DDRTLQ (SEQ ID NO:3).

In embodiments, the first domain comprises, or consists of, an amino acid sequence having at least 65, 70, 75, 80, 85, 90 or 95% sequence similarity with the sequence GSAKPGNGSYF (SEQ ID NO: 41).

In embodiments, the first domain comprises, or consists of, an amino acid sequence having one amino acid substitution relative to the sequence PDDRTLQ (SEQ ID NO:1) DDRTLQ (SEQ ID NO:3) or GSAKPGNGSYF (SEQ ID NO: 41).

In embodiments, the first domain comprises, or consists of, an amino acid sequence having one amino acid substitution relative to the sequence PDDRTLQ (SEQ ID NO:1) or DDRTLQ (SEQ ID NO:3). In embodiments, the first domain comprises, or consists of, the sequence PDDRTLQ (SEQ ID NO:1) or DDRTLQ (SEQ ID NO:3).

In embodiments, the first domain comprises, or consists of, an amino acid sequence having one amino acid substitution relative to the sequence GSAKPGNGSYF (SEQ ID NO: 41).

In embodiments, the first domain comprises, or consists of, the sequence GSAKPGNGSYF (SEQ ID NO: 41)

In embodiments, the second domain comprises, or consists of, an amino acid sequence having one amino acid substitution relative to the sequence QNPVYLIPETVPYIKWDN (SEQ ID NO:2) or SVKTEMLGNEID (SEQ ID NO: 29).

In embodiments, the second domain comprises, or consists of, an amino acid sequence having one amino acid substitution relative to the sequence QNPVYLIPETVPYIKWDN (SEQ ID NO:2). In embodiments, the second domain comprises, or consists of, the sequence QNPVYLIPETVPYIKWDN (SEQ ID NO:2).

In embodiments, the second domain comprises, or consists of, an amino acid sequence having one amino acid substitution relative to the sequence SVKTEMLGNEID (SEQ ID NO: 29). In embodiments, the second domain comprises, or consists of, the sequence SVKTEMLGNEID (SEQ ID NO: 29).

In an embodiment, the substitution is a conservative substitution, i.e. for an amino acid having similar structure and/or physico-chemical properties. Conservative substitution tables are well known in the art (see for example Creighton (1984) Proteins. W. H. Freeman and Company (Eds)), and representative examples of conservative substitutions are depicted in Table I below.

TABLE I

Examples of conserved amino acid substitutions

| Residue | Conservative Substitutions |
|---|---|
| Ala | Ser |
| Arg | Lys |

TABLE I-continued

| Examples of conserved amino acid substitutions | |
|---|---|
| Residue | Conservative Substitutions |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

Covalent modifications of the peptide are also included within the scope of the present invention. Such modifications may be introduced into the peptide for example by reacting targeted amino acid residues of the peptide with an organic derivatizing agent that is capable of reacting with selected side chains or terminal residues. The following examples of chemical derivatives are provided by way of illustration and not by way of limitation.

Cysteinyl residues may be reacted with alpha-haloacetates (and corresponding amines), such as 2-chloroacetic acid or chloroacetamide, to give carboxymethyl or carboxyamidomethyl derivatives. Histidyl residues may be derivatized by reaction with compounds such as diethylprocarbonate e.g., at pH 5.5-7.0 because this agent is relatively specific for the histidyl side chain, and para-bromophenacyl bromide may also be used; e.g., where the reaction is preferably performed in 0.1M sodium cacodylate at pH 6.0. Lysinyl and amino terminal residues may be reacted with compounds such as succinic or other carboxylic acid anhydrides. Other suitable reagents for derivatizing alpha-amino-containing residues include compounds such as imidoesters, e.g. methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues is typically performed in alkaline conditions because of the high pKa of the guanidine functional group. Furthermore, these reagents may react with the groups of lysine as well as the arginine epsilon-amino group. The specific modification of tyrosinyl residues per se is well-known, such as for introducing spectral labels into tyrosinyl residues by reaction with aromatic diazonium compounds or tetranitromethane. N-acetylimidazol and tetranitromethane may be used to form 0-acetyl tyrosinyl species and 3-nitro derivatives, respectively.

Carboxyl side groups (aspartyl or glutamyl) may be selectively modified by reaction with carbodiimides (R'—N═C═N—R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions. Glutaminyl and asparaginyl residues may be frequently deamidated to the corresponding glutamyl and aspartyl residues. Other modifications of the peptides in the present invention may include hydroxylation of proline and lysine, phosphorylation of hydroxyl groups of seryl or threonyl residues, methylation of the alpha-amino groups of lysine, arginine, and histidine side chains acetylation of the N-terminal amine, methylation of main chain amide residues (or substitution with N-methyl amino acids) and, in some instances, amidation of the C-terminal carboxyl groups, according to known method steps.

Covalent attachment of fatty acids (e.g., $C_6$-$C_{18}$) to the peptides may confer additional biological properties such as protease resistance, plasma protein binding, increased plasma half-life, intracellular penetration, etc. The above description of modification of a peptide does not limit the scope of the approaches nor the possible modifications that can be engineered.

In embodiments, the first domain of the peptide may be covalently linked to the second domain either directly (e.g., through a peptide bond) or via a suitable linker moiety, e.g., a linker of one or more amino acids (e.g., a glycine linker, a alanine linker, a linker comprising a mixture of amino acids) or another type of chemical linker (e.g., a carbohydrate linker, a lipid linker, a fatty acid linker, a polyether linker, PEG, etc. (see, e.g., Hermanson (1996) Bioconjugate techniques). In an embodiment, one or more additional domain(s) may be inserted between the first and second domains (e.g., the first and/or second domain(s) may be duplicated in the peptide). In an embodiment, the first and second domains are covalently linked through a linker of one or more amino acids, in a further embodiment an amino acid linker of 1 to 10 amino acids or 1 to 5 amino acids, for example a linker of 1, 2, 3, 4 or 5 amino acids. In an embodiment, the linker comprises one or more alanine and/or leucine residues, in a further embodiment the linker is A or LA.

In embodiments, the first and second domains may be linked C-terminus to N-terminus, C-terminus to C-terminus, N-terminus to N-terminus, or N-terminus to C-terminus. In an embodiment, each of the first domain and the second domain has an N-terminal amino acid and a C-terminal amino acid, and the C-terminal amino acid of the first domain is covalently linked to the N-terminal amino acid of the second domain. In an embodiment, the first domain is N-terminal to the second domain.

In embodiments, the N- and/or C-terminal amino acids of the peptide may be modified by amidation, acetylation, acylation or other modifications known in the art. In an embodiment, the amino terminal residue (i.e., the free amino group at the N-terminal end of the peptide) of the peptide is modified (e.g., for protection against degradation). In an embodiment, the modification is acylation with a $C_2$-$C_{16}$ acyl group, in a further embodiment, the modification is acetylation. In another embodiment, the amino terminal residue is not modified (e.g., it comprises the native $NH_2$ group).

In an embodiment, the carboxy terminal residue (i.e., the free carboxy group at the C-terminal end of the peptide) of said peptide is modified (e.g., for protection against degradation). In an embodiment, the modification is an amidation. In another embodiment, the carboxy terminal residue is not modified (e.g., it comprises the native COOH group).

In an embodiment, the first domain comprises from about 5 to about 9 or from about 6 to about 8 amino acids, i.e., 5, 6, 7, 8 or 9 amino acids, preferably 6, 7 or 8 amino acids and more preferably 7.

In an embodiment, the second domain comprises from about 13 to about 23 or from about 15 to about 21 amino acids, i.e., 13, 14, 15, 16, 17, 18, 19, 20, 21, 22 or 23 amino acids, preferably 15, 16, 17, 18, 19, 20 or 21 amino acids, more preferably 18.

In an embodiment, the above-mentioned peptide contains about 100 amino acids or less. In a further embodiment, the above-mentioned peptide contains about 90 amino acids or less. In a further embodiment, the above-mentioned peptide contains about 80 amino acids or less. In a further embodiment, the above-mentioned peptide contains about 70 amino acids or less. In a further embodiment, the above-mentioned peptide contains about 60 amino acids or less. In a further embodiment, the above-mentioned peptide contains about 50 amino acids or less. In a further embodiment, the above-mentioned peptide contains about 40 amino acids or less. In a further embodiment, the above-mentioned peptide contains about 30 amino acids or less. In a further embodiment, the above-mentioned peptide contains between about 20 to about 30 amino acids, for example 21, 22, 23, 24, 25, 26, 27, 28 or 29 amino acids.

In an embodiment, the peptide comprises, or consists of, the amino acid sequence DDRTLQLAQNPVYLIPETVPYIKWDN (SEQ ID NO: 4) or GSAKPGNGSYFASVKTEMLGNEID (SEQ ID NO: 27). In an embodiment, the peptide comprises, or consists of, the amino acid sequence DDRTLQLAQNPVYLIPETVPYIKWDN (SEQ ID NO: 4). In another embodiment, the peptide comprises, or consists of, the amino acid sequence GSAKPGNGSYFASVKTEMLGNEID (SEQ ID NO: 27).

The present invention further includes pharmaceutically acceptable salts of the above-mentioned peptide.

The peptide of the invention may be produced by expression in a host cell comprising a nucleic acid encoding the peptide (recombinant expression) or by chemical synthesis (e.g., solid-phase peptide synthesis). Peptides can be readily synthesized by automated solid phase procedures well known in the art. Suitable syntheses can be performed by utilizing "T-boc" or "Fmoc" procedures. Techniques and procedures for solid phase synthesis are described in for example *Solid Phase Peptide Synthesis: A Practical Approach*, by E. Atherton and R. C. Sheppard, published by IRL, Oxford University Press, 1989. Alternatively, the peptides may be prepared by way of segment condensation, as described, for example, in Liu et al., *Tetrahedron Lett.* 37: 933-936, 1996; Baca et al., *J. Am. Chem. Soc.* 117: 1881-1887, 1995; Tam et al., *Int. J. Peptide Protein Res.* 45: 209-216, 1995; Schnolzer and Kent, *Science* 256: 221-225, 1992; Liu and Tam, *J. Am. Chem. Soc.* 116: 4149-4153, 1994; Liu and Tam, *Proc. Natl. Acad. Sci. USA* 91: 6584-6588, 1994; and Yamashiro and Li, *Int. J. Peptide Protein Res.* 31: 322-334, 1988). Other methods useful for synthesizing the peptides are described in Nakagawa et al., *J. Am. Chem. Soc.* 107: 7087-7092, 1985. Commercial providers of peptide synthetic services may also be used to prepare synthetic peptides in the D- or L-configuration. Such providers include, for example, Advanced ChemTech (Louisville, Ky.), Applied Biosystems (Foster City, Calif.), Anaspec (San Jose, Calif.), and Cell Essentials (Boston, Mass.).

Peptides comprising naturally occurring amino acids encoded by the genetic code may also be prepared using recombinant DNA technology using standard methods. Peptides produced by recombinant technology may be modified (e.g., N-terminal acylation [e.g., acetylation], C-terminal amidation, cyclization/formation of a loop within the peptide [e.g., via formation of a disulphide bridge between Cys residues]) using methods well known in the art. Therefore, in embodiments, in cases where a peptide described herein contains naturally occurring amino acids encoded by the genetic code, the peptide may be produced using recombinant methods, and may in embodiments be subjected to for example the just-noted modifications (e.g., acylation, amidation, cyclization). Accordingly, in another aspect, the invention further provides a nucleic acid encoding the above-mentioned peptide. The invention also provides a vector comprising the above-mentioned nucleic acid. In yet another aspect, the present invention provides a cell (e.g., a host cell) comprising the above-mentioned nucleic acid and/or vector. The invention further provides a recombinant expression system, vectors and host cells, such as those described above, for the expression/production of a peptide of the invention, using for example culture media, production, isolation and purification methods well known in the art.

Such vectors comprise a nucleic acid sequence capable of encoding such a peptide operably linked to one or more transcriptional regulatory sequence(s). In an embodiment, the peptide is a fusion peptide containing a domain which facilitates its purification (e.g., His-tag, GST-tag). Nucleic acids may be introduced into cells for expression using standard recombinant techniques for stable or transient expression. Nucleic acid molecules may include any chain of two or more nucleotides including naturally occurring or non-naturally occurring nucleotides or nucleotide analogues.

"Recombinant expression" refers to the production of a peptide or polypeptide by recombinant techniques, wherein generally, a nucleic acid encoding peptide or polypeptide is inserted into a suitable expression vector which is in turn used to transform/transfect a host cell to produce the protein. The term "recombinant" when made in reference to a protein or a polypeptide refers to a peptide, polypeptide or protein molecule which is expressed using a recombinant nucleic acid construct created by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as "recombinant" therefore indicates that the nucleic acid molecule has been manipulated using genetic engineering, i.e., by human intervention. Recombinant nucleic acid constructs may for example be introduced into a host cell by transformation/transfection. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

The term "vector" refers to a nucleic acid molecule, which is capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors".

A recombinant expression vector of the present invention can be constructed by standard techniques known to one of ordinary skill in the art and found, for example, in Sambrook et al. (1989) in *Molecular Cloning: A Laboratory Manual*. A variety of strategies are available for ligating fragments of DNA, the choice of which depends on the nature of the termini of the DNA fragments and can be readily determined by persons skilled in the art. The vectors of the present invention may also contain other sequence elements to facilitate vector propagation and selection in bacteria and host cells. In addition, the vectors of the present invention may comprise a sequence of nucleotides for one or more restriction endonuclease sites. Coding sequences such as for selectable markers and reporter genes are well known to persons skilled in the art.

A recombinant expression vector comprising a nucleic acid sequence of the present invention may be introduced into a host cell, which may include a living cell capable of expressing the protein coding region from the defined recombinant expression vector. The living cell may include both a cultured cell and a cell within a living organism. Accordingly, the invention also provides host cells containing the recombinant expression vectors of the invention. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (*Molecular Cloning: A Laboratory Manual*, $2^{nd}$ Edition, Cold Spring Harbor Laboratory press (1989)), and other laboratory manuals. Methods for introducing DNA into mammalian cells in vivo are also known, and may be used to deliver the vector of the invention to a subject for gene therapy.

"Transcriptional regulatory sequence/element" is a generic term that refers to DNA sequences, such as initiation and termination signals, enhancers, and promoters, splicing signals, polyadenylation signals which induce or control transcription of protein coding sequences with which they are operably linked. A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences. Generally, operably-linked DNA sequences are contiguous and, where necessary to join two protein coding regions, in reading frame. However, since for example enhancers generally function when separated from the promoters by several kilobases and intronic sequences may be of variable lengths, some polynucleotide elements may be operably-linked but not contiguous.

As used herein, the term "transfection" or "transformation" generally refers to the introduction of a nucleic acid, e.g., via an expression vector, into a recipient cell by nucleic acid-mediated gene transfer.

A cell (e.g., a host cell or indicator cell), tissue, organ, or organism into which has been introduced a foreign nucleic acid (e.g., exogenous or heterologous DNA [e.g. a DNA construct]), is considered "transformed", "transfected", or "transgenic". A transgenic or transformed cell or organism also includes progeny of the cell or organism and progeny produced from a breeding program employing a transgenic organism as a parent and exhibiting an altered phenotype resulting from the presence of a recombinant nucleic acid construct. A transgenic organism is therefore an organism that has been transformed with a heterologous nucleic acid, or the progeny of such an organism that includes the transgene. The introduced DNA may be integrated into chromosomal DNA of the cell's genome, or alternatively may be maintained episomally (e.g., on a plasmid). Methods of transfection are well known in the art (see for example, Sambrook et al., 1989, supra; Ausubel et al., 1994 supra).

For stable transfection of mammalian cells, it is known that, depending upon the expression vector and transfection technique used, only a small fraction of cells may integrate the foreign DNA into their genome. In order to identify and select these integrants, a gene that encodes a selectable marker (such as resistance to antibiotics) may be introduced into the host cells along with the gene of interest. As used herein, the term "selectable marker" is used broadly to refer to markers which confer an identifiable trait to the indicator cell. Non-limiting example of selectable markers include markers affecting viability, metabolism, proliferation, morphology and the like. Preferred selectable markers include those that confer resistance to drugs, such as G418, hygromycin and methotrexate. Nucleic acids encoding a selectable marker may be introduced into a host cell on the same vector as that encoding the peptide compound or may be introduced on a separate vector. Cells stably transfected with the introduced nucleic acid may be identified by drug selection (cells that have incorporated the selectable marker gene will survive, while the other cells die).

The peptides of the invention can be purified by many techniques well known in the art, such as reverse phase chromatography, high performance liquid chromatography (HPLC), ion exchange chromatography, size exclusion chromatography, affinity chromatography, gel electrophoresis, and the like. The actual conditions used to purify a particular peptide or peptide analog will depend, in part, on synthesis strategy and on factors such as net charge, hydrophobicity, hydrophilicity, and the like, and will be apparent to those of ordinary skill in the art. For affinity chromatography purification, any antibody which specifically binds the peptide may for example be used.

In an embodiment, the above-mentioned peptide is substantially pure. A compound is "substantially pure" when it is separated from the components that naturally accompany it. Typically, a compound is substantially pure when it is at least 60%, more generally 75%, preferably over 90% and more preferably over 95, 96, 97, 98 or 99% by weight, of the total material in a sample. Thus, for example, a polypeptide that is chemically synthesized or produced by recombinant technology will generally be substantially free from its naturally associated components. A nucleic acid molecule is substantially pure when it is not immediately contiguous with (i.e., covalently linked to) the coding sequences with which it is normally contiguous in the naturally occurring genome of the organism from which the DNA of the invention is derived. A substantially pure compound can be obtained, for example, by extraction from a natural source; by expression of a recombinant nucleic acid molecule encoding a polypeptide compound; or by chemical synthesis. Purity can be measured using any appropriate method such as column chromatography, gel electrophoresis, HPLC, etc.

In embodiments, the present invention provides a peptide comprising any combination/subcombination of the features or properties defined herein.

In embodiments, the present invention provides a composition comprising a peptide of sequence (A) and a peptide of sequence (B) as defined above.

In another aspect, the present invention also provides a pharmaceutical composition comprising the above-described peptide (i.e. a peptide of sequence (A) and/or a peptide of sequence (B) as defined above) and a pharmaceutically acceptable carrier or excipient.

As used herein "pharmaceutically acceptable carrier" or "excipient" includes any and all solvents, dispersion media, coatings, antibacterial and antifungal agents, isotonic and absorption delaying agents, and the like that are physiologically compatible. In an embodiment, the carrier is suitable for parenteral administration. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds/compositions of the invention include ethylenevinyl acetate copolymer particles, osmotic pumps, implantable infusion systems, and liposomes. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

In another aspect, the present invention also provides a vaccine or immunogenic composition comprising the above-described peptide (i.e. a peptide of sequence (A) and/or a peptide of sequence (B) as defined above). In an embodiment, the vaccine or immunogenic composition further comprises a vaccine adjuvant.

"Immunogenic composition" or "vaccine" as used herein refers to a composition or formulation comprising the above-mentioned peptide or a vaccine vector. Vaccination methods for treating or preventing infection (e.g., EBV infection) in a mammal comprise use of a vaccine or vaccine vector to be administered by any conventional route known in the vaccine field, e.g., via a mucosal (e.g., ocular, intranasal, pulmonary, oral, gastric, intestinal, rectal, vaginal, or urinary tract) surface, via a parenteral (e.g., subcutaneous, intradermal, intramuscular, intravenous, or intraperitoneal) route, or topical administration (e.g., via a transdermal delivery system such as a patch).

"Adjuvant" refers to a substance which, when added to an immunogenic agent such as an antigen, nonspecifically enhances or potentiates an immune response to the agent in the host upon exposure to the mixture. "Adjuvant", "immunostimulatory" and "immunopotentiating" activity as used refers to an increase in the immune response/reaction to the peptide due to the adjuvant, i.e. relative to the immune response/reaction when the peptide is used alone. Examples of adjuvants currently used in the field of vaccines include (1) mineral salts (aluminum salts such as aluminum phosphate and aluminum hydroxide, calcium phosphate gels), squalene, (2) oil-based adjuvants such as oil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), (3) particulate adjuvants, e.g., virosomes (unilamellar liposomal vehicles incorporating influenza haemagglutinin), AS04 ([SBAS4] aluminum salt with MPL), ISCOMS (structured complex of saponins and lipids), polylactide co-glycolide (PLG), (4) microbial derivatives (natural and synthetic), e.g., monophosphoryl lipid A (MPL), Detox (MPL+*M. Phlei* cell wall skeleton), AGP [RC-529] (synthetic acylated monosaccharide), DC_Chol (lipoidal immunostimulators able to self-organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects), (5) endogenous human immunomodulators, e.g., hGM-CSF or hIL-12 (cytokines that can be administered either as protein or plasmid encoded), Immudaptin (C3d tandem array) and/or (6) inert vehicles, such as gold particles.

In another aspect, the present invention provides an isolated antibody or an antigen-binding fragment thereof that specifically recognizes the peptide defined herein (i.e. a peptide of sequence (A) and/or a peptide of sequence (B) as defined above), wherein said antibody is not antibody clone 72A1 or an antibody comprising the complement determining regions (CDRs) of antibody clone 72A1. The CDRs of antibody clone 72A1 are disclosed, for example, in PCT publication No. WO2013/130565 and comprises the following amino acids: Heavy chain CDR1: GSSFTDYT (SEQ ID NO: 36); Heavy chain CDR2: INPYNGGT (SEQ ID NO: 37); Heavy chain CDR3: AGGLRRVNWFAY (SEQ ID NO: 38); Light chain CDR1: TGAVTTSNY (SEQ ID NO: 39); Light chain CDR2: GTN; and Light chain CDR3: VLWHSNHWV (SEQ ID NO: 40).

The term "antibody or antigen-binding fragment thereof" as used herein refers to any type of antibody/antibody fragment including monoclonal antibodies (including full-length monoclonal antibodies), polyclonal antibodies, multispecific antibodies, humanized anitbodies, CDR-grafted antibodies, chimeric antibodies and antibody fragments so long as they exhibit the desired antigenic specificity/binding activity. Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, $V_H$ regions ($V_H$, $V_H$-$V_H$), anticalins, PepBodies, antibody-T-cell epitope fusions (Troybodies) or Peptibodies.

The term "monoclonal antibody" as used herein refers to an antibody from a population of substantially homogeneous antibodies, i.e., the individual antibodies comprising the population are substantially similar and bind the same epitope(s), except for possible variants that may arise during production of the monoclonal antibody, such variants generally being present in minor amounts. Such monoclonal antibody typically includes an antibody comprising a variable region that binds a target, wherein the antibody was obtained by a process that includes the selection of the antibody from a plurality of antibodies. For example, the selection process can be the selection of a unique clone from a plurality of clones, such as a pool of hybridoma clones, phage clones or recombinant DNA clones. It should be understood that the selected antibody can be further altered, for example, to improve affinity for the target, to humanize the antibody, to improve its production in cell culture, to reduce its immunogenicity in vivo, to create a multispecific antibody, etc., and that an antibody comprising the altered variable region sequence is also a monoclonal antibody of this invention. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including the hybridoma method (e.g., Kohler et al., Nature, 256:495 (1975); Harlow et al., Antibodies: A Laboratory Manual, (Cold Spring Harbor Laboratory Press, 2nd ed. 1988); Hammerling et al., in: Monoclonal Antibodies and T-Cell Hybridomas 563-681, (Elsevier, N.Y., 1981), recombinant DNA methods (see, e.g., U.S. Pat. No. 4,816,567), phage display technologies (see, e.g., Clackson et al., Nature, 352:624-628 (1991); Marks et al., J. Mol. Biol., 222:581-597 (1991); Sidhu et al., J. Mol. Biol. 338(2):299-310 (2004); Lee et al., J. Mol. Biol. 340(5): 1073-1093 (2004); Fellouse, Proc. Nat. Acad. Sci. USA 101(34): 12467-12472 (2004); and Lee et al. J. Immunol. Methods 284(1-2):119-132 (2004) and technologies for producing human or human-like antibodies from animals that have parts or all of the human immunoglobulin loci or genes encoding human immunoglobulin sequences (see, e.g., WO98/24893, WO96/34096, WO96/33735, and WO91/10741, Jakobovits et al., Proc. Natl. Acad. Sci. USA, 90:2551 (1993); Jakobovits et al., Nature, 362:255-258 (1993); Bruggemann et al., Year in Immune, 7:33 (1993); U.S. Pat. Nos. 5,545,806, 5,569,825, 5,591,669 (all of GenPharm); U.S. Pat. No. 5,545,807; WO 97/17852, U.S. Pat. Nos. 5,545,807; 5,545,806; 5,569,825; 5,625,126; 5,633,425; and 5,661,016, and Marks et al., Bio/Technology, 10: 779-783 (1992); Lonberg et al., Nature, 368: 856-859 (1994); Morrison, Nature, 368: 812-813 (1994); Fishwild et al., Nature Biotechnology, 14: 845-851 (1996); Neuberger, Nature Biotechnology, 14: 826 (1996); and Lonberg and Huszar, Intern. Rev. Immunol., 13: 65-93 (1995). Antibodies capable of specifically binding to the peptide defined herein can also be produced using phage display technology. Antibody fragments that selectively bind to peptide defined herein can then be isolated. Exemplary methods for producing such antibodies via phage display are disclosed, for example, in U.S. Pat. No. 6,225,447.

In another embodiment, the antibody is a "chimeric" or "recombinant" antibody, i.e. an antibody in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 (1984)). Chimeric antibodies of interest herein include "primatized" antibodies comprising variable domain antigen-binding sequences derived from a non-human primate (e.g., Old World Monkey, Ape, etc.) and human constant region sequences, as well as "humanized" antibodies.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region (e.g., a complementary-determining region, CDR) of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). Human chimeric antibody and human CDR-grafted antibody may be prepared using methods known in the art.

In other aspects, the present invention provides one or more nucleic acids encoding the variable region of the light and/or heavy chain of the above-mentioned antibody, as well as vector(s) comprising the one or more nucleic acids.

In another aspect, the present invention provides a method of inducing the production of neutralizing antibodies against a gp350-expressing herpesvirus in an animal, said method comprising administering an effective amount of the above-mentioned peptide (i.e. a peptide of sequence (A) and/or a peptide of sequence (B) as defined above) or composition to said animal.

In another aspect, the present invention provides a method of immunizing or vaccinating an animal against a gp350-expressing herpesvirus, said method comprising administering an effective amount of the above-mentioned peptide (i.e. a peptide of sequence (A) and/or a peptide of sequence (B) as defined above) or composition to said animal.

In another aspect, the present invention provides the use of the above-mentioned peptide (i.e. a peptide of sequence (A) and/or a peptide of sequence (B) as defined above) or composition for inducing the production of neutralizing antibodies against a gp350-expressing herpesvirus in an animal.

In another aspect, the present invention provides the use of the above-mentioned peptide (i.e. a peptide of sequence (A) and/or a peptide of sequence (B) as defined above) or composition for the preparation of a medicament for inducing the production of neutralizing antibodies against a gp350-expressing herpesvirus in an animal.

In another aspect, the present invention provides the use of the above-mentioned peptide (i.e. a peptide of sequence (A) and/or a peptide of sequence (B) as defined above) or composition for immunizing or vaccinating an animal against a gp350-expressing herpesvirus in an animal.

In another aspect, the present invention provides the use of the above-mentioned peptide (i.e. a peptide of sequence (A) and/or a peptide of sequence (B) as defined above) or composition for the preparation of a medicament for immunizing or vaccinating an animal against a gp350-expressing herpesvirus in an animal.

The term "gp350-expressing herpesvirus" refers to a herpesvirus that expresses a glycoprotein similar in structure and function to the Epstein-Barr virus (EBV) major virion surface glycoprotein gp350/220. Herpesviruses known to express such a glycoprotein include EBV, Kaposi Sarcoma-associated herpesvirus (KSHV), murine gamma herpesvirus 68 (glycoprotein 150), murid herpesvirus-4, Wood mouse herpesvirus, and rhesus lymphocryptovirus (Macacine herpesvirus-4). In an embodiment, the gp350-expressing herpesvirus is a gammaherpesvirus, for example a lymphocryptovirus, in a further embodiment EBV.

In view of the fact that EBV causes infectious mononucleosis and plays a role in the emergence of two rare forms of cancer, namely Burkitt's lymphoma and nasopharyngeal carcinoma, the present invention also relates to the prevention and/or treatment of infectious mononucleosis, Burkitt's lymphoma and/or nasopharyngeal carcinoma using the above-mentioned peptide or composition.

The peptide (i.e. a peptide of sequence (A) and/or a peptide of sequence (B) as defined above) or composition of the present invention may be used for both prophylactic and therapeutic purposes. As used herein, "treatment" is an approach for obtaining beneficial or desired results, including clinical results. For purposes of this invention, beneficial or desired clinical results include, but are not limited to (i) alleviation or amelioration of one or more symptoms, (ii) diminishment of extent of disease, (iii) stabilizing (i.e., not worsening) state of disease, (iv) preventing spread of disease, (v) delay or slowing of disease progression, (vi) amelioration or palliation of the disease state, and (vii) remission (whether partial or total), whether detectable or undetectable. "Treatment" can also mean prolonging survival as compared to expected survival if not receiving treatment. Treatment may be effected in a single dose or repeated at intervals. The appropriate dosage depends on various parameters understood by skilled artisans such as the vaccine or vaccine vector itself, the route of administration or the condition of the mammal to be vaccinated (weight, age, gender, and the like). As used herein, "prevention" refers to an approach for causing the clinical symptoms not to develop, to develop later or to develop in a less severe infection/disease, e.g., preventing disease/infection from occurring and/or developing to a harmful state.

An "effective amount" of a substance (peptide) is that amount sufficient to effect beneficial or desired results, including clinical results, and, as such, an "effective amount" depends upon the context in which it is being applied. In the context of administering a peptide or composition of the present invention, an effective amount is, for example, an amount sufficient to achieve a modulation (quantitative and/or qualitative) of the immune response, notably an increase in the levels of neutralizing antibodies directed against the gp350 antigen. An effective amount can be administered in one or more administration(s).

The invention further provides a kit or package comprising the above-mentioned peptide (i.e. a peptide of sequence (A) and/or a peptide of sequence (B) as defined above) or the above-mentioned composition, together with instructions for (i) inducing the production of neutralizing antibodies against a gp350-expressing herpesvirus in an animal (ii) for immunizing or vaccinating an animal against a gp350-expressing herpesvirus.

In another aspect, the present invention provides a method for detecting the presence or absence neutralizing antibodies against a gp350-expressing herpesvirus in a sample, the method comprising contacting the sample with the above-mentioned peptide (i.e. a peptide of sequence (A) and/or a peptide of sequence (B) as defined above), and detecting the presence or absence of neutralizing antibodies/peptide complexes.

Methods to measure the amount/level of antibodies (e.g., anti-gp350 neutralizing antibodies) are well known in the art. Antibody levels may be detected either directly using the peptide of the present invention. The peptide may be labeled/conjugated, e.g., radio-labeled, chromophore-labeled, fluorophore-labeled, or enzyme-labeled to facilitate detection and quantification of the complex (direct detection). Alternatively, the peptide/neutralizing antibodies complex may be detected using a second ligand specifically recognizing the first ligand (indirect detection). Such second ligand may be radio-labeled, chromophore-labeled, fluorophore-labeled, or enzyme-labeled to facilitate detection and quantification of the complex. Enzymes used for labelling antibodies for immunoassays are known in the art, and the most widely used are horseradish peroxidise (HRP) and alkaline phosphatase (AP).

Examples of methods to measure the amount/level of anti-gp350 neutralizing antibodies using the peptide of the present invention include, but are not limited to: Western blot, immunoblot, enzyme-linked immunosorbant assay (ELISA), radioimmunoassay (RIA), immunoprecipitation, surface plasmon resonance (SPR), chemiluminescence, antibody array, microscopy or flow cytometry.

In an embodiment, the level of anti-gp350 neutralizing antibodies within the methods of the present invention is determined using by an immunoassay (e.g., ELISA), for example using the peptide of the invention and anti-IgG antibodies. In an embodiment, the peptide of the invention is immobilized on a solid support, such as magnetic or chromatographic matrix particles, the surface of an assay plate (such as microtiter wells), pieces of a solid substrate material (such as plastic, nylon, paper), and the like. The biological sample (e.g., serum) of the subject is then put in contact with the solid support coated with the peptide of the invention so that the anti-gp350 neutralizing antibodies present in the sample binds to the attached peptide. The solid support may be washed one or more times, and a ligand (which is preferably labelled to facilitate detection) recognizing the anti-gp350 neutralizing antibodies (e.g., an anti-Ig antibody or a fragment thereof) is put in contact with the coated solid support to measure the amount of anti-gp350 neutralizing antibodies bound to the plate (which is representative of the level of anti-gp350 neutralizing antibodies present in the sample). The amount of ligand recognizing the anti-gp350 neutralizing antibodies (e.g., an anti-Ig antibody or a fragment thereof) is determined using any methods known in the art, for example radiometric-, colorimetric-, fluorometric- or enzymatic-based methods. Thus, the solid support will contain labels in proportion to the amount of secondary antibody bound to the plate. If the label is an enzyme (e.g., HRP, AP), a substrate for the enzyme may be applied, and catalysis by the enzyme leads to a measurable signal, for example a change in color or fluorescence, which may be measured using a spectrometer, for example (or any other device capable of detecting changes in color or fluorescence). The intensity of the signal is indicative of or proportional to the amount of the anti-gp350 neutralizing antibodies in the sample, and may be compared to a control. The intensity of the signal may be transformed into a corresponding anti-gp350 neutralizing antibody level using a known standard (i.e. based on the signal obtained with a sample that contains a known concentration of anti-gp350 neutralizing antibodies or a plurality of such samples to establish a standard curve).

As used herein the term “animal” refers for example to a mammal including human, mice, rat, dog, cat, pig, cow, monkey, horse, etc. In an embodiment, the above-mentioned animal is a mammal, in a further embodiment a human.

MODE(S) FOR CARRYING OUT THE INVENTION

The present invention is illustrated in further details by the following non-limiting examples.

Example 1: Materials and Methods

Cell Culture.

The EBV producing cell line P3HR1 (HTB-62, American Type Culture Collection (ATCC), Manassas, Va.), the anti-gp350 hybridoma 72A1 (HB-168, ATCC), the Burkitt cell line Raji (CCL-86, ATCC) and the T cell line CEM (HTB-45, ATCC) were maintained in RPMI-1640 supplemented with 10% heat-inactivated FBS and antibiotics. The Chinese hamster ovary cell line CHO-K1 (CCL-61, ATCC) was grown in Kiaghn’s F-12K medium supplemented with 10% FBS and antibiotics.

Peptide Sequencing.

The amino-terminal amino acid sequences of the 72A1 antibody heavy and light chains were determined by Edman degradation (kindly performed by Dr Claude Lazure, Institut de Recherche Clinique de Montréal, Montréal, QC) following antibody purification by Protein-A affinity chromatography, resolution of the antibody heavy and light chain peptides in a denaturing 12% PAGE gel and transfer to a PVDF membrane.

Cloning of the Heavy and Light Variable Regions.

Hybridoma heavy and light chain mRNA sequences were cloned using protocols outlined in Jones and Barnard (13) or Yuan et al (40). Briefly, total RNA was isolated from hybridoma cells using Tri reagent (Molecular Research Center®, Cincinnati, Ohio), followed by ethanol precipitation and suspension in RNase-free water (Invitrogen® Canada, Burlington, ON). cDNA strands were initially generated using the Enhanced Avian RT First Strand® Kit (Sigma-Aldrich® Canada, Oakville, ON) and primers encoding the conserved heavy or light chain J-sequences JHRC (5'-CTGAGGAGACGGTGACCATGGTCCCTTG-GCCCC-3', SEQ ID NO: 10) and JκRC (5'-CGTTT-GATTTCCAGCTTGGTCCC-3', SEQ ID NO: 11), respectively (13). Subsequent PCR amplification of the heavy and light chain variable region cDNA sequences was performed using AccuPrime® Pfx DNA polymerase (Invitrogen Canada) in conjunction with heavy or light chain variable region degenerate primer sets (6,15,40). In order to differentiate authentic light chain variable region cDNA from endogenous aberrant κ-chain mRNA (3) 1.7-fold excess (175 μM) aberrant-chain-specific primer (5'-ACCTAT-TACTGTCAGCACATTA-3', SEQ ID NO: 12) was added to the PCR reaction mix (40). This was expected to preferentially amplify the aberrant κ chain and produce a smaller PCR product that allows for identification of authentic antibody light chain variable region cDNA products. Authentic heavy chain cDNAs generated by PCR were identified by screening for the presence of aberrant heavy chain transcripts (10). Authentic heavy and light chain cDNAs were cloned into pCR-BLUNT-II TOPO® vector (Invitrogen® Canada, Burlington, ON) for subsequent DNA sequencing.

Construction and Expression of a Human-Mouse Chimeric Anti-gp350 IgG1 Antibody.

Human IgG1 heavy chain and human K chain constant region cDNAs were obtained by RT-PCR amplification of peripheral blood lymphocyte RNA using primers that encode the amino terminal amino acids WGQGTMVTVS-SAST (SEQ ID NO: 13) of the human IgG heavy chain constant region (5'-TGGGGCCAAGGGACAATGGTCAC-CGTCTCTTCAGCCTCCACC-3', SEQ ID NO: 14), the terminal IgG amino acids (5'-TCATTTACCCGGAGACA-GGGAG-3', SEQ ID NO: 15), the amino terminal amino acids GTKLEIK (SEQ ID NO: 35) of the human Ig κ chain constant region (5'-GGGACCAAGCTGGAAATCAAACG-3', SEQ ID NO: 16) and the terminal Ig κ chain amino acids (5'-CTCCCTCTAACACTCTCCCCTG-3', SEQ ID NO: 17). Following in-frame ligation of the 72A1 heavy and light chain variable regions to their respective human Ig constant regions, the chimeric heavy and light chain antibody cDNAs were cloned into eukaryotic expression plasmids pHooK-3 and pcDNA3.1, respectively, allowing for selection of G418- and Zeocin-resistant cells.

CHO-K1 cells were dual transfected with chimeric light chain and heavy chain expression plasmids using Lipofectamine® 2000 (Invitrogen®), plated in culture medium containing 500 μg/ml G-418 and 300 μg/ml Zeocin and, after three weeks of culture, individual colonies were isolated and tested for chimeric IgG1 antibody reactivity to gp350. Gp350-expressing CEM cells, generated following transfection of the gp350 expression plasmid pCMVIE-EBMA (38), were used as a substrate to measure and confirm gp350 reactivity. Gp350 reactivity was measured by fixed cell immunofluorescence and by flow cytometry analysis.

EBV Antibody Neutralization Assay.

Antibody neutralization potency was measured as the inhibition of EBV early antigen (EA) expression upon super-infection of Raji cells by P3HR1 virus (33). Mixtures of concentrated virus ($2\times10^4$ EA-inducing units) and serial dilutions of purified antibody were incubated in a final volume of 0.1 ml for 60 min at 37° C. prior to the addition of $5\times10^4$ Raji cells. The Raji cell-virus mixture was further incubated for 60 min at 37° C. followed by resuspension in RPMI medium and a 2-day incubation at 37° C. The number of Raji cells expressing EA after cell culture was measured by immunofluorescence, and relative antibody neutralization potency per μg of antibody was calculated.

In Silico Identification of the Gp350 Neutralization Domain.

The gp350/220 neutralization domain was identified by aligning 72A1 variable region protein sequences with the previously reported 3D structure for the gp350 amino-terminal peptide (31). Identification of the complementarity determining regions (CDR) of the 72A1 antibody was based on previously described methods (19). The 3D structure of the 72A1 antibody variable region was generated by the Web Antibody Modeling server (http://antibody.bath.ac.uk/index.html, Dr. A. R. Rees, Centre for Protein Analysis and Design, University of Bath, UK; Whitelegg, N. R. J. and Rees, A. R (2000). WAM—an improved algorithm for modelling antibodies on the Web. *Prot. Eng.,* 13, 819-824) and the Rosetta Antibody Modeling Server (http://antibody.graylab.jhu.edu) (29). 72A1 antibody:gp350 protein docking was performed using SnugDock (28) and compared with lysozyme:gp350 docking that serves as an irrelevant docking control protein.

Peptide and Whole Cell ELISA.

Gp350 mimetic peptides that were synthesized and HPLC purified to >70% (Elim Biopharmaceuticals®, Hayward, Calif.) were suspended at 2.5 μg/mL in 0.1M carbonate buffer pH 9 prior to their overnight incubation at 4° C. as 100 μL aliquots in a 96 well ELISA plate (Ultident®, St. Laurent, QC). Peptide-coated plates were washed 4× with PBS: 0.05% Tween-20®, blocked with 1% BSA:PBS and incubated for a minimum of 2 h at room temperature (RT) with anti-gp350 monoclonal antibody 72A1, or the isotype-matched, background-control anti-LMP1 monoclonal antibody S-12 and 1:100 dilutions of commercial intravenous gamma globulin (IVIG) (18). Bound monoclonal antibodies were detected using biotin-conjugated goat anti-mouse IgG, biotin-conjugated anti-human IgG and horseradish peroxidase (HRP)-conjugated streptavidin (Jackson Immunoresearch Laboratories®, West Grove, Pa.) in conjunction with 3,3',5,5'-Tetramethylbenzidine substrate (TMB solution, Bioshop®, Burlington ON). HRP enzyme activity was stopped with an equal volume of 1N HCl and wells read at $450_{nm}$.

Whole cell ELISA was performed using CEM cells or CEM cells expressing gp350. The cells were washed with PBS, suspended at $1\times10^6$ cells/mL in PBS and 40 μL aliquots were added to each ELISA plate well. Plates were vacuum-dried prior to cell fixation with cold methanol. Plates were washed with PBS and wells blocked in 1% BSA:PBS prior to a 1 h exposure to monoclonal antibody or monoclonal antibody that was pre-incubated for 2 or more hours with gp350 mimetic peptides. Bound monoclonal antibodies were detected using biotin-conjugated goat anti-mouse IgG, HRP-conjugated streptavidin as outlined above.

Peptide Immunization.

Balb/C female mice were immunized intraperitoneally with 100 μg of keyhole limpet hemocyanin (KLH)-coupled with gp350 mimetic peptide (Sigma Conjugation Kit) emulsified in Sigma Adjuvant System (Sigma-Aldrich). Mice were re-injected every 21 days and blood was drawn 14 days after the second injection. Following the third immunization, IgG levels of peptide reactivity were measured by ELISA.

Example 2: Identification and Functional Validation of Cloned 72A1 Fab Sequences Previous epitope mapping of gp350 indicates one dominant neutralizing epitope and the target of the neutralizing monoclonal antibody 72A1 (31,33,37). The heavy and light chain variable region RNA sequences for this antibody were cloned and sequenced, and it was verified that cloned cDNA sequences encoding the amino-terminal peptide sequences of the two chains matched those of both the mature heavy and light chain proteins (FIG. 1, top two panels). The amino acid sequences predicted from the cloned heavy and light chain variable region RNA sequences, along with predicted complementarity determining regions (CDR, bold), and peptides noted after Edman degradation sequencing are shown in the top two panels of FIG. 1. A space-filled, 3D PDB model of the 72A1 variable region and its CDRs, generated from Web and Rosetta antibody modeling programs and from predicted variable region peptides, is depicted in the bottom panel of FIG. 1.

Protein BLAST comparison of 72A1 variable region peptides with the monoclonal antibody peptides listed in the non-redundant (nr) database of the National Center for Biotechnology Information (ncbi.nlm.nih.gov) showed a >98% sequence identity with several monoclonal antibodies for both the heavy and light chain variable regions. For the 72A1 light chain peptide, a >98% identity with the anti-human tumor-associated antigen monoclonal antibody [Genbank accession # AAA39002], the anti-carcinoma-associated antigen monoclonal antibody 17-1A [Genbank accession # AAA38774], and the anti-flavivirus monoclonal antibody Fab4g2 [Genbank accession #1 UYW_L] was noted. Analysis of the 72A1 heavy chain variable peptide showed a >98% identity with that of MopC21 (14). This suggests that in addition to recognizing the neutralization epitope of gp350, the murine heavy chain may also act as an Ig scaffold to better position the 72A1 light chain (12).

Figure 2B:
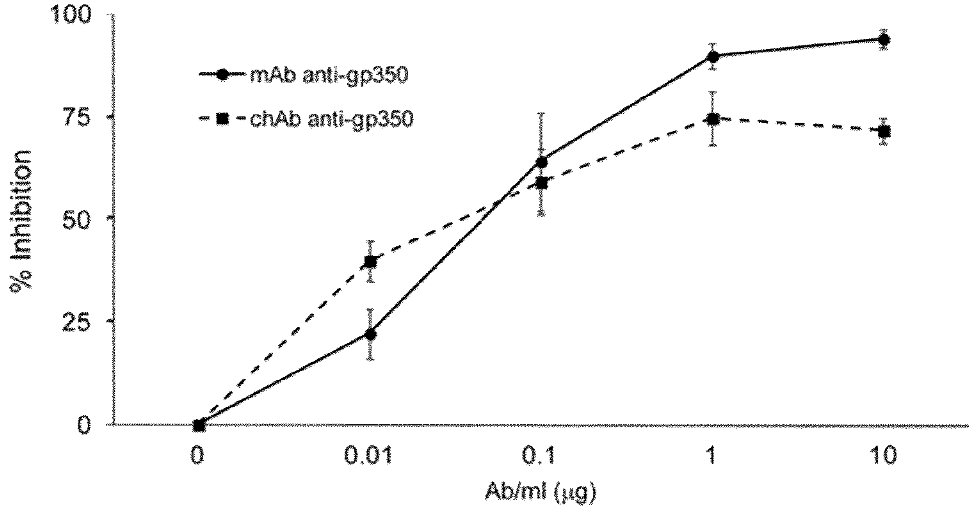

In order to verify that the authentic 72A1 variable region RNAs were faithfully cloned and functional, a human-mouse chimeric antibody containing the 72A1 variable region sequences that were fitted in-frame to a human IgG1 constant region (FIG. 1, top panels) was constructed. The chimeric antibody was functionally tested and compared to murine 72A1 for both gp350 recognition and for virus neutralization. As measured by fixed cell immunofluorescence, flow cytometry analysis or a culture-based EBV neutralization assay, the chimeric anti-gp350 monoclonal faithfully recognized cell-surface gp350 (FIG. 2A) and blocked P3HR1 EBV super-infection of Raji cells on par with that of the murine version of 72A1 when tested at $\log_{10}$ dilutions of 0.01 to 10 μg/ml (FIG. 2B). These results authenticated the procedures used, such that the mRNAs encoding the 72A1 monoclonal antibody were shown to be faithfully cloned and functional.

Example 3: Identification of the Gp350 Neutralization Domain

In silico identification of the gp350/220 neutralization domain was performed by spatially aligning the 72A1 variable region peptide sequences with the amino-terminal portion of gp350 using the SnugDock algorithm (28,31). The SnugDock molecular docking program predicts the optimal alignment for close coupling of the 72A1 variable region with the gp350 molecule by identifying the lowest energy structure between two molecules along with notation of the solvent accessible residues. The SnugDock program also lists the interfacing residues and ones that would form hydrogen or disulfide bonds, a salt bridge or a covalent link (28). SnugDock alignment indicated that the gp350 amino terminus couples to 72A1 variable region through four interfacing peptide sequences, namely $_{14}$QLTRDDP$_{20}$ (SEQ ID NO: 30), $_{144}$QNPVYLIPETVPYIKWDN$_{161}$ (SEQ ID NO: 2), $_{194}$SVKTEMLGNEIDIECIME$_{211}$ (SEQ ID NO: 18) and $_{288}$KASG$_{291}$ (SEQ ID NO: 19). Other individual amino acids on the surface of the gp350 molecule also align closely with the 72A1 antibody binding site and include lysine$_{106}$, the glutamine pair $Q_{118}Q_{119}$, phenylalaninem and threonine$_{228}$. In conjunction with the weaker covalence formed between the four gp350 coupling peptides and the 72A1 variable region, individual amino acids in these four peptides are predicted to contribute stronger H-bonding or to form a salt bridge (Table II). The listing of those amino acids on the surface of gp350 that interact with the 72A1 heavy and light chain variable region along with a corresponding spatial depiction is shown in FIG. 3.

TABLE II

| Anti-gp350 variable region interaction with soluble gp350 | | |
|---|---|---|
| Location | CDR Amino Acid Sequence | Predicted gp350: 72A1 Amino Acid Bonding |
| LC-CDR1 | KAS**EN**VVT**Y**VS (SEQ ID NO: 20) | GLU$_{27}$-H-GLN$_{144}$<br>ASN$_{28}$-H-ASN$_{145}$ |
| LC-CDR2 | GASNRYT (SEQ ID NO: 21) | No association found |
| LC-CDR3 | GQ**GYSYP**YT (SEQ ID NO: 22) | TYR$_{92}$-H-LEU$_{15}$<br>TYR$_{94}$-H-ASP$_{18}$ |
| HC-CDR1 | **FT**F**SSF**GMH (SEQ ID NO: 23) | SER$_{31}$-H-SER$_{290}$ |
| HC-CDR2 | **ISSGSSTLHYAD**TV**K**GRF (SEQ ID NO: 24) | SER$_{52}$-H-ASP$_{205}$<br>THR$_{57}$-H-ASP$_{205}$<br>LYS$_{65}$-H-GLU$_{118}$ |
| HC-CDR3 | **WGNYPH**YAMDY (SEQ ID NO: 25) | GLY$_{100}$-H-ARG$_{17}$<br>TRY$_{102}$-H-LYS$_{196}$<br>PRO$_{103}$-H-SER$_{194}$<br>HIS$_{104}$ +/- GLU$_{211}$ |
| LC-FW | **QL**VMT (SEQ ID NO: 26) | LEU$_{2}$-H-TYR$_{148}$ |

LC, light chain; HC, heavy chain; FW, frame work; CDR, complementarity determining region; Bold, interfacing residue; H, hydrogen bond; +/- salt bridge. Amino acid numbering was derived from 72A1 mature heavy and light chain peptide sequences depicted in FIG. 1 and the gp350 amino terminal peptide sequence depicted in FIG. 3.

Example 4: Gp350 Peptide Mimetic Blocks 72A1 Binding to Gp350

Figure 4A:
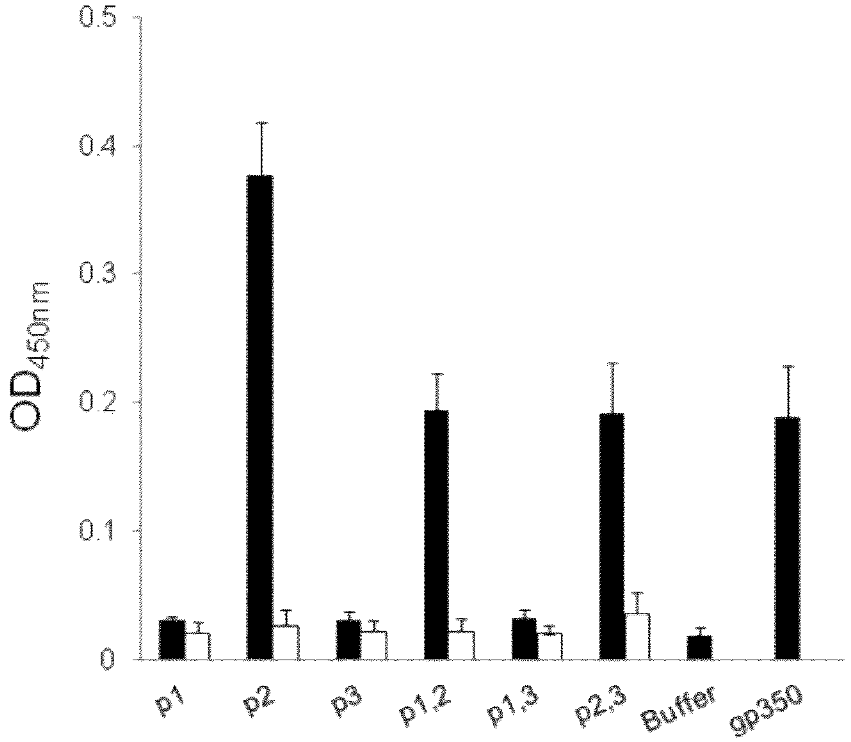
FIGS. 4A and 4B show that Gp350 mimetic peptide binds to 72A1 antibody to block gp350 recognition.

In order to validate the gp350 amino acids found by SnugDock alignment to couple with the 72A1 antibody variable region (Table II), two gp350 mimetic peptides that would correctly spatially-position those gp350 amino acids predicted by SnugDock to interact with the 72A1 antibody variable region (FIG. 3) were designed. Peptide 3 (p3) mimetic, GSAKPGNGSYFASVKTEMLGNEID (SEQ ID NO: 27) encompassed the central area of the purported gp350 neutralizing domain (FIG. 3, peptide domains 3 and 4) and was comprised in part of an inverted form of the gp350 sequence $_{282}$FYSGNGPKASG$_{292}$ (SEQ ID NO: 28) spatially joined with an alanine linked (A) to gp350 sequence $_{194}$SVKTEMLGNEID$_{205}$ (SEQ ID NO: 29). Peptide 2 (p2) DDRTLQLAQNPVYLIPETVPYIKWDN (SEQ ID NO: 4) encompassed the perimeter portion of the gp350 neutralizing domain (FIG. 3, peptide domains 1 and 2) and contained an inverted amino acid form of gp350 sequence $_{14}$QLTRDDP$_{20}$ (SEQ ID NO: 30) (the proline (P) residue was removed solely to increase the peptide yield during synthesis) spatially joined via a leucine-alanine (LA) linker to gp350 sequence $_{144}$QNPVYLIPETVPYIK-WDN$_{161}$ (SEQ ID NO: 2). The gp350 linear peptide (p1)$_{422}$SKAPESTTTSPTLNTTGFADY$_{441}$ (SEQ ID NO: 31), which was previously shown to lie outside the gp350 neutralizing domain and expected not to bind to the 72A1 antibody (31,37), was also used. As shown in FIG. 4A, peptide 2 strongly bound to the 72A1 antibody, whereas peptide 3 and peptide 1 did not bind to the 72A1 antibody. The binding of 72A1 antibody to peptide 2 appeared specific as the monoclonal antibody S-12, which recognizes an intracellular epitope on the EBV LMP-1 protein, did not bind to peptide 2 (FIG. 4A).

Figure 4B:
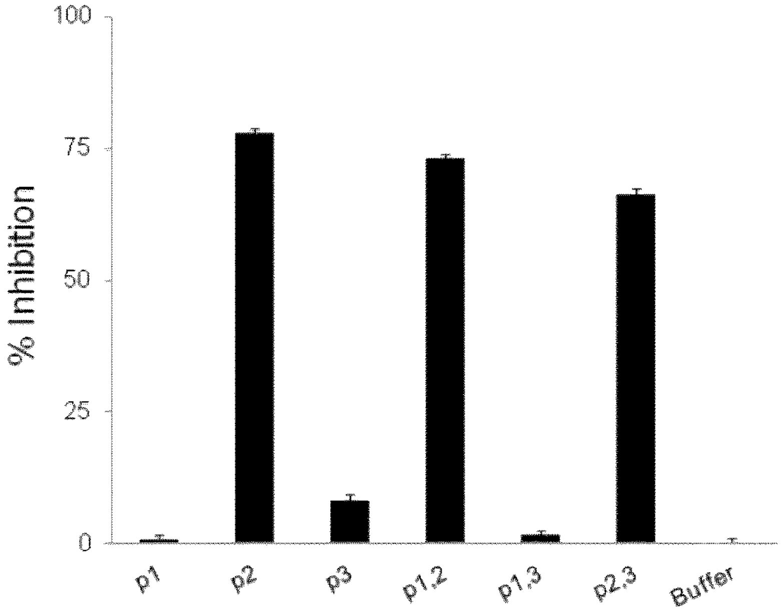

Although peptide 3 contained the amino acid sequence EID shown by mutation to result in a loss of 72A1 binding (31), the lack of noted binding by peptide 3 may have been due to inappropriate adsorption to the ELISA plate that interfered with antibody binding. To avoid potential ELISA plate interference, gp350 mimetic peptides were allowed to interact with 72A1 antibody in solution, and later the antibody was tested for its ability to bind to native gp350 protein. As shown in FIG. 4B, peptide 2 strongly competed for the 72A1 antibody binding site and inhibited antibody recognition of gp350 protein by 78% (p1 versus p2, p=0.04). Peptide 3 did not appear to bind to the 72A1 antibody as it blocked 72A1 recognition of gp350 protein by only 8% (FIG. 4B, p3). It also appeared that mimetic peptide 2 comprised the principal elements of the 72A1 binding domain as incubation of 72A1 with peptide 2 and 3 did not significantly change inhibition levels seen by peptide 2 alone (FIG. 4B, 78% for p2 versus 66% for p2,3).

Figure 4C:
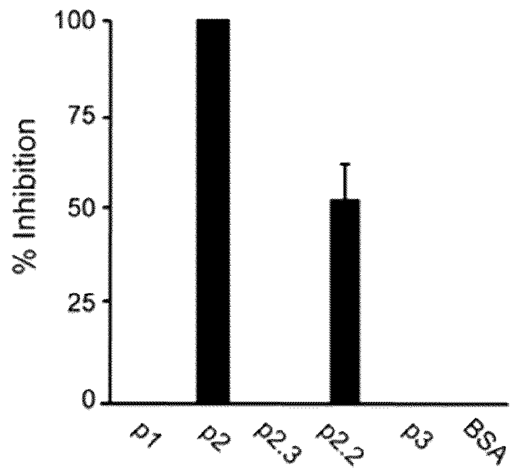
FIG. 4C shows that Gp350 mimetic peptide (p) 2, p2.3 and p2.2 block virus neutralizing, anti-gp350 monoclonal antibody recognition of mature gp350 protein in an ELISA assay. Percent inhibition was plotted as average inhibition±SEM, and was derived from duplicate samples and from three separate experiments.

In order to define whether gp350 epitope domain 1, domain 2 or both domains of p2 contributed to the maximal epitope recognition by the 72A1 antibody, each domain was altered and compared to peptide 2 (p2) for recognition by the 72A1 antibody. As shown in FIG. 4C, alteration of gp350 domain 2 as found in p2.3 abolished recognition of p2 by 72A1 antibody. Alteration of gp350 domain 1 as found in p2.2 resulted in a 50% reduction in recognition of p2 by 72A1 antibody. These results indicate that amino acid sequences found in p2 domain 1 and p2 domain 2 contribute to maximum epitope recognition by the virus neutralizing, anti-gp350 antibody 72A1.

Figure 5:
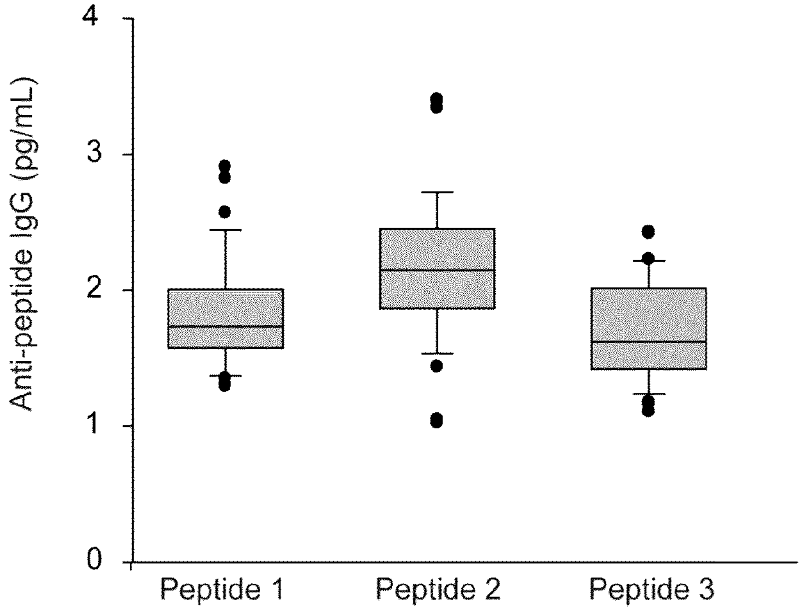
FIG. 5 shows that gamma globulin reacts with gp350 mimetic peptides. Anti-peptide antibody concentrations are depicted as a box-and-whiskers plot with sample values outside the first percentile and $99^{th}$ percentile (●). Plot values were calculated from duplicate samples in three separate experiments using 39 different lots of intravenous immunoglobulin.

Although p2 was recognized by the murine monoclonal antibody 72A1 and was capable of generating antibodies that recognized the gp350 neutralizing epitope in mice, it is unknown whether EBV-positive human sera would recognize this gp350 mimetic peptide. The determination of human IgG reactivity against each of the three peptides could serve as a surrogate indicator of whether the gp350 mimetic peptides would be immunogenic or capable of generating an anti-gp350 antibody response. The mimetic peptides, when assayed with human EBV immune serum derived from thirty-nine unique lots of IVIG (each representative of >1000 healthy blood donor units) (41, 42), revealed that all three peptides were recognized (FIG. 5). Peptide 2 exhibited the highest antibody levels at 2.16±0.08 SD pg/ml. This was followed by p1 at levels of 1.83±0.07 pg/ml and by p3 with antibody levels of 1.7±0.06 pg/ml. These results suggest that anti-gp350 antibodies found in a large segment of the population recognize the gp350 mimetic peptides.

To further map the anti-gp350 reactivity of the 72A1 monoclonal antibody, the ELISA reactivity of the peptides depicted in Table III below with the 72A1 monoclonal antibody was tested.

TABLE III

| Peptides tested for their reactivity with the 72A1 monoclonal antibody | | |
|---|---|---|
| Gp350 peptide | Sequence | Notes |
| Peptide 1 | SKAPESTTTSPTLNT TGFADY (SEQ ID NO: 31) | 72A1 non-reactive |

TABLE III-continued

| Peptides tested for their reactivity with the 72A1 monoclonal antibody | | |
|---|---|---|
| Gp350 peptide | Sequence | Notes |
| Peptide 2 | **DDRTLQ***LA*QNPVYLI PETVPYIKWDN (SEQ ID NO: 4) | Full-length 72A1 epitope **Domain 1**-*LA*-Domain 2 |
| Peptide 2.1 | EEKSAEAAQQPADAA PDSAPDAKMDQ (SEQ ID NO: 32) | 72a1 positive mimeotope |
| Peptide 2.2 | **AAAAAAAAQNPVYLI PETVPYIKWDN** (SEQ ID NO: 33) | Ala substitution of domain 1 AAAAA-A-domain 2 |
| Peptide 2.3 | **DDRTLQL**AAAPVAAL IPAVVPAIAWAA (SEQ ID NO: 34) | **Domain 1**-*LA*-altered Domain 2 |

Figure 6A:
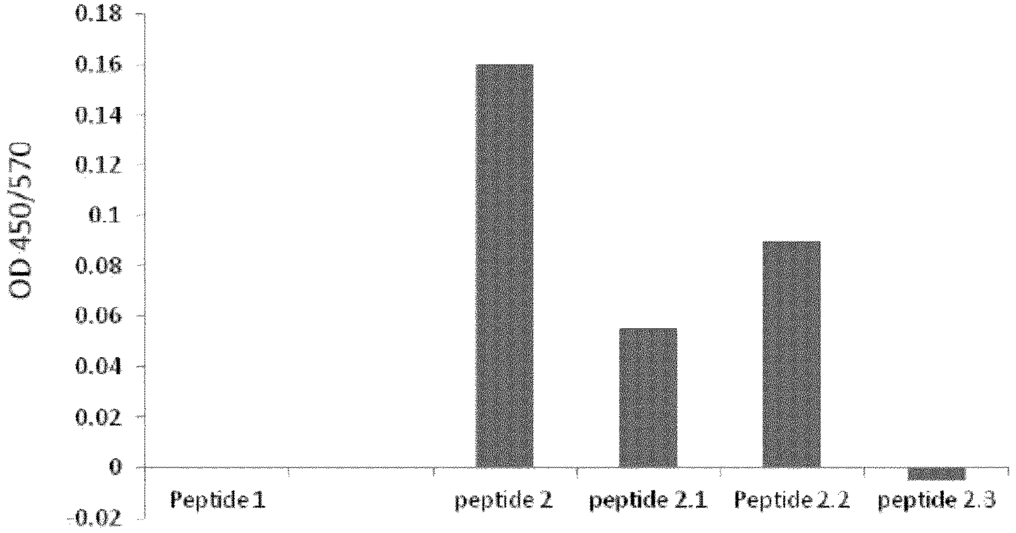
FIG. 6A shows an average ELISA reactivity with the anti-gp350 neutralizing antibody 72A1. Peptide 1 ELISA activity (OD=0.355) was subtracted from the peptide 2 series before plotting.
Figure 6B:
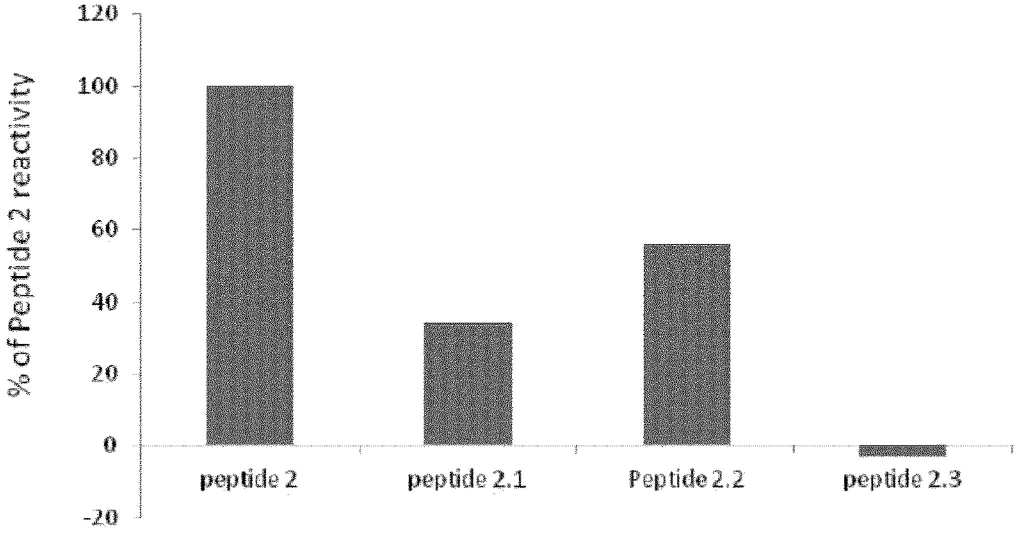
FIG. 6B shows the percentage of 72A1 reactivity to peptide 2 series after alanine substitutions. Peptide 2 was given the default value of 100%.

The results depicted in FIGS. 6A and 6B show that peptide 2.2, which contains an alanine-substituted domain 1 and native domain 2 of peptide 2, binds to a lesser extent to the 72A1 monoclonal antibody as compared to peptide 2 (i.e. 56% binding activity compared to parental peptide 2, FIG. 6B). Peptide 2.3, which contains several alanine substitutions in domain 2 and native domain 1 of peptide 2, did not bind to the 72A1 monoclonal antibody. These results show that although domain 1 of peptide 2 does not appear to significantly bind to the 72A1 antibody in the absence of native domain 2, it seems to increase or facilitate the binding of domain 2 to the 72A1 antibody, and/or to cooperate with domain 2 for binding to the 72A1 antibody.

Figure 7A:
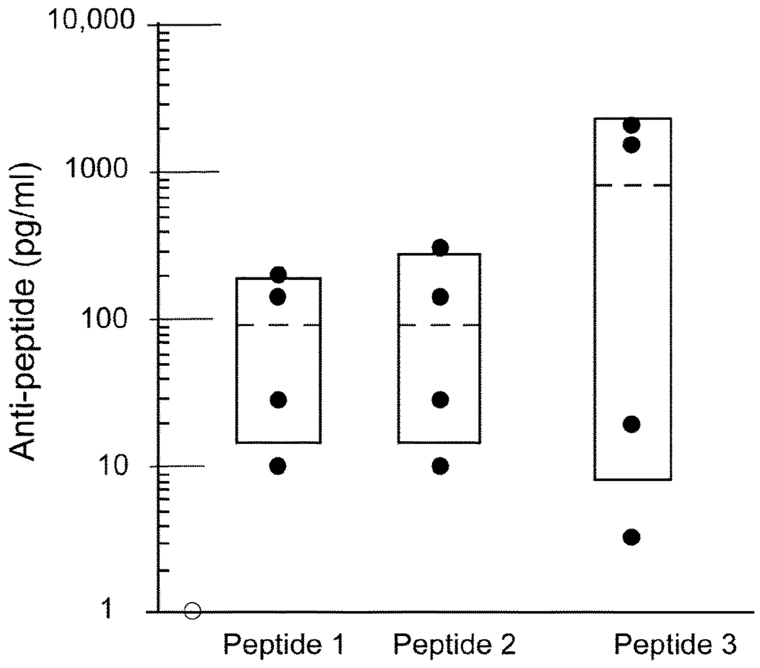
FIG. 7A shows that Gp350 peptide 1, peptide 2 and peptide 3 generate antibodies in mice. Box plot showing anti-peptide antibody concentration found in peptide-immunized mice. Preimmune serum recognition of peptide is indicated (○).
Figure 7B:
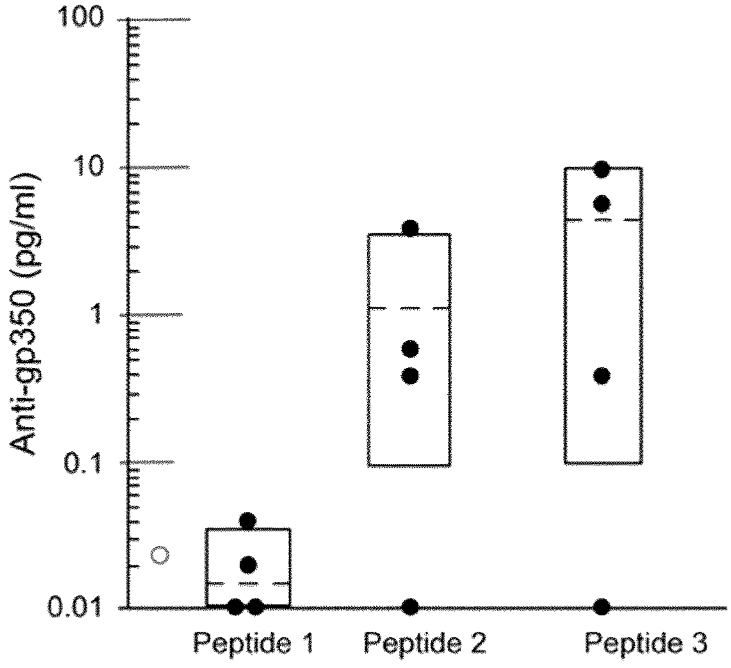
FIG. 7B shows that Gp350 peptides generate antibodies in mice that recognize gp350 protein. Box plot of anti-gp350 concentration found in peptide-immunized mice. Preimmune serum recognition of peptide or gp350 is indicated (○).

Example 5: Gp350 Mimetic Peptides Elicit Gp350 Cross-Reactive Antibodies and is Recognized by Human IgG Balb/C female mice were immunized intraperitoneally with gp350 mimetic peptides as described in Example 1 above. Following the third immunization, IgG levels of peptide reactivity were measured by ELISA. All mice generated antibodies to their respective peptides with average antibody concentrations (pg/ml) of 97±46 SEM, 122±67 and 981±577 for p1, p2 and p3, respectively (FIG. 7A). When these same mice sera were assayed for recognition of native gp350, results revealed a 2-$\log_{10}$ reduction in antibody titers, with average antibody concentrations (pg/ml) of 0.015±0.01 SEM, 1.3±0.9 and 4.1±2.4 for p1, p2 and p3, respectively (FIG. 7B). Assays to determine whether sera from peptide-immunized mice have the ability to interfere with 72A1 recognition of gp350 indicated that p2- and p3-derived antisera were capable of inhibiting 72A1 recognition of gp350 by 38% and 23%, respectively (FIG. 7C). Pooled sera from both p2 and p3 immunized mice resulted in an additive reduction of 51% in 72A1 antibody recognition of gp350 (FIG. 7C).

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. American Cancer Society. American Cancer Society. Global Cancer Facts and FIGS. 299 2nd Edition. 2011. Atlanta.
2. Buchwald, D. S., T. D. Rea, W. J. Katon, J. E. Russo, and R. L. Ashley. 2000. Acute infectious mononucleosis: characteristics of patients who report failure to recover. 303 *Am. J. Med.* 109:531-537. doi:S0002-9343(00) 00560-X [pii].
3. Carroll, W. L., E. Mendel, and S. Levy. 1988. Hybridoma fusion cell lines contain an aberrant kappa transcript. *Mol. Immunol.* 25:991-995.
4. Cohen, J. I., A. S. Fauci, H. Varmus, and G. J. Nabel. 2011. Epstein-Barr virus: an important vaccine target for cancer prevention. *Sci. Transl. Med.* 3:107fs7. doi:3/107/107fs7 [pii]; 10.1126/scitranslmed.3002878 [doi].
5. Cohen, J. I., E. S. Mocarski, N. Raab-Traub, L. Corey, and G. J. Nabel. 2013. The need and challenges for development of an Epstein-Barr virus vaccine. *Vaccine* 31 Suppl 2:B194-B196. doi:S0264-410X(12)01361-8 [pii]; 10.1016/j.vaccine.2012.09.041 [doi].
6. Coloma, M. J., A. Hastings, L. A. Wims, and S. L. Morrison. 1992. Novel vectors for the expression of antibody molecules using variable regions generated by polymerase chain reaction. *J. Immunol. Methods* 152:89-104.
7. Finerty, S., M. Mackett, J. R. Arrand, P. E. Watkins, J. Tarlton, and A. J. Morgan. 1994. Immunization of cottontop tamarins and rabbits with a candidate vaccine against the Epstein-Barr virus based on the major viral envelope glycoprotein 318 gp340 and alum. *Vaccine* 12:1180-1184. doi:0264-410X(94)90240-2 [pii].
8. Henle, G., W. Henle, and V. Diehl. 1968. Relation of Burkitt's tumor-associated herpes-type virus to infectious mononucleosis. *Proc. Natl. Acad. Sci. U.S.A.* 59:94-101.
9. Hoffman, G. J., S. G. Lazarowitz, and S. D. Hayward. 1980. Monoclonal antibody against a 250,000-dalton glycoprotein of Epstein-Barr virus identifies a membrane antigen and a neutralizing antigen. *Proc. Natl. Acad. Sci. U.S.A.* 77:2979-2983.
10. Irani, Y., M. Tea, R. G. Tilton, D. J. Coster, K. A. Williams, and H. M. Brereton. 2008. PCR amplification of the functional immunoglobulin heavy chain variable gene from a hybridoma in the presence of two aberrant transcripts. *J. Immunol. Methods* 336:246-250.
11. Jagadeesh, D., B. A. Woda, J. Draper, and A. M. Evens. 2012. Post transplant lymphoproliferative disorders: risk, classification, and therapeutic recommendations. *Curr. Treat. Options. Oncol.* 13:122-136. doi:10.1007/s11864-011-0177-x [doi].
12. Johnson, J. K., D. M. Cerasoli, and D. E. Lenz. 2005. Role of immunogen design in induction of soman-specific monoclonal antibodies. *Immunol. Lett.* 96:121-127.
13. Jones, M. L. and R. T. Barnard. 2005. Chimerization of multiple antibody classes using splice overlap extension PCR. *Biotechniques* 38:181-182.
14. Kearney, J. F., A. Radbruch, B. Liesegang, and K. Rajewsky. 1979. A new mouse myeloma cell line that has lost immunoglobulin expression but permits the construction of antibody-secreting hybrid cell lines. *J. Immunol.* 123:1548-1550.
15. Krebber, A., S. Bornhauser, J. Burmester, A. Honegger, 339 J. Willuda, H. R. Bosshard, and A. Pluckthun. 1997. Reliable cloning of functional antibody variable domains from hybridomas and spleen cell repertoires employing a reengineered phage display system. *J. Immunol. Methods* 201:35-55.

16. Kumar, R. N., S. L. Hass, J. Z. Li, D. J. Nickens, C. L. Daenzer, and L. K. Wathen. 2003. Validation of the Health-Related Productivity Questionnaire Diary (HRPQ-D) on a sample of patients with infectious mononucleosis: results from a phase 1 multicenter clinical trial. *J. Occup. Environ. Med.* 45:899-907. doi:10.1097/01.jom.0000083039.56116.79 [doi].
17. Luzuriaga, K. and J. L. Sullivan. 2010. Infectious mononucleosis. *N. Engl. J. Med.* 362:1993-2000. doi:362/21/1993 [pii]; 10.1056/NEJMcp1001116 [doi].
18. Mann, K. P., D. Staunton, and D. A. Thorley-Lawson. 1985. Epstein-Barr virus encoded protein found in plasma membranes of transformed cells. *J. Virol.* 55:710-720.
19. Martin, A. C. R. 2009. Antibodies. http://www.bioinf.org.uk/index.html MacCallum, R. M., Martin, A. C. R. and Thornton, J. T. Antibody-antigen interactions: Contact analysis and binding site topography. *J. Mol. Biol.* 262, 732-745
20. McDonald, R. A., J. M. Smith, M. Ho, R. Lindblad, D. Ikle, P. Grimm, R. Wyatt, M. Arar, D. Liereman, N. Bridges, and W. Harmon. 2008. Incidence of PTLD in pediatric renal transplant recipients receiving basiliximab, calcineurin inhibitor, sirolimus and steroids. *Am. J. Transplant.* 8:984-989. doi:AJT2167 [pii]; 10.1111/j.1600-6143.2008.02167.x [doi].
21. Miller, G., L. Heston, and G. Hoffman. 1982. Neutralization of lymphocyte immortalization by different strains of Epstein-Barr virus with a murine monoclonal antibody. *Infect. Immun.* 37:1028-1031.
22. Nemerow, G. R., R. A. Houghten, M. D. Moore, and N. R. Cooper. 1989. Identification of an epitope in the major envelope protein of Epstein-Barr virus that mediates viral binding to the B lymphocyte EBV receptor (CR2). *Cell* 56:369-377.
23. Odumade, O. A., K. A. Hogquist, and H. H. Balfour, Jr. 2011. Progress and problems in understanding and managing primary Epstein-Barr virus infections. *Clin. Microbiol. Rev.* 24:193-209. doi:24/1/193 [pii]; 10.1128/CMR.00044-10 [doi].
24. Ogembo, J. G., L. Kannan, I. Ghiran, A. Nicholson-Weller, R. W. Finberg, G. C. Tsokos, and J. D. Fingeroth. 2013. Human complement receptor type 1/CD35 is an Epstein-Barr Virus receptor. *Cell Rep.* 3:371-385. doi:S2211-1247(13)00030-2 [pii]; 10.1016/j.celrep.2013.01.023 [doi].
25. Qualtiere, L. F., J. F. Decoteau, and M. Hassan Nasr-el-Din. 1987. Epitope mapping of the major Epstein-Barr virus outer envelope glycoprotein gp350/220. *J. Gen. Virol.* 68 (Pt 2):535-543.
26. Raab-Traub, N. 2012. Novel mechanisms of EBV-induced oncogenesis. *Curr. Opin. Virol* 2:453-458. doi:S1879-6257(12)00106-X [pii]; 10.1016/j.coviro.2012.07.001 [doi].
27. Rees, L., E. J. Tizard, A. J. Morgan, W. D. Cubitt, S. Finerty, T. A. Oyewole-Eletu, K. Owen, C. Royed, S. J. Stevens, R. C. Shroff, M. K. Tanday, A. D. Wilson, J. M. Middeldorp, P. L. Amlot, and N. M. Steven. 2009. A phase I trial of epstein-barr virus gp350 vaccine for children with chronic kidney disease awaiting transplantation. *Transplantation* 88:1025-1029. doi:10.1097/TP.0b013e3181b9d918 381 [doi]; 00007890-200910270-00013 [pii].
28. Sircar, A. and J. J. Gray. 2010. SnugDock: Paratope Structural Optimization during Antibody-Antigen Docking Compensates for Errors in Antibody Homology Models. *PLoS. Compt. Biol.* 6:e1000644.1-e1000644.13.
29. Sircar, A., E. Kim, and J. J. Gray. 2009. Rosetta Antibody: Antibody variable region homology modeling. *Nucleic Acids Res.* 37:W474-W479.
30. Sokal, E. M., K. Hoppenbrouwers, C. Vandermeulen, M. Moutschen, P. Leonard, A. Moreels, M. Haumont, A. Bollen, F. Smets, and M. Denis. 2007. Recombinant gp350 vaccine for infectious mononucleosis: a phase 2, randomized, double-blind, placebo-controlled trial to evaluate the safety, immunogenicity, and efficacy of an Epstein-Barr virus vaccine in healthy young adults. *J. Infect. Dis.* 196:1749-1753. doi:10.1086/523813 [doi].
31. Szakonyi, G., M. G. Klein, J. P. Hannan, K. A. Young, R. Z. Ma, R. Asokan, V. M. Holers, and X. S. Chen. 2006. Structure of the Epstein-Barr virus major envelope glycoprotein. *Nat. Struct. Mol. Biol.* 13:996-1001.
32. Tanner, J., J. Weis, D. Fearon, Y. Whang, and E. Kieff. 1987. Epstein-Barr virus gp350/220 binding to the B lymphocyte C3d receptor mediates adsorption, capping, and endocytosis. *Cell* 50:203-213.
33. Tanner, J., Y. Whang, J. Sample, A. Sears, and E. Kieff. 1988. Soluble gp350/220 and deletion mutant glycoproteins block Epstein-Barr virus adsorption to lymphocytes. *J. Virol.* 62:4452-4464.
34. Tanner, J. E. and C. Alfieri. 1999. Epstein-Barr virus induces 403 Fas (CD95) in T cells and Fas ligand in B cells leading to T-cell apoptosis. *Blood* 94:3439-3447.
35. Tanner, J. E., C. Alfieri, T. A. Chatila, and F. Diaz-Mitoma. 1996. Induction of interleukin-6 after stimulation of human B-cell CD21 by Epstein-Barr virus glycoproteins gp350 and gp220. *J. Virol.* 70:570-575.
36. Thorley-Lawson, D. A. and K. Geilinger. 1980. Monoclonal antibodies against the major glycoprotein (gp350/220) of Epstein-Barr virus neutralize infectivity. *Proc. Natl. Acad. Sci. U.S.A.* 77:5307-5311.
37. Urquiza, M., R. Lopez, H. Patino, J. E. Rosas, and M. E. Patarroyo. 2005. Identification of three gp350/220 regions involved in Epstein-Barr virus invasion of host cells. *J. Biol. Chem.* 280:35598-35605. doi:M504544200 [pii]; 10.1074/jbc.M504544200 [doi].
38. Whang, Y., M. Silberklang, A. Morgan, S. Munshi, A. B. Lenny, R. W. Ellis, and E. Kieff. 1987. Expression of the Epstein-Barr virus gp350/220 gene in rodent and primate cells. *J. Virol.* 61:1796-1807.
39. Young, K. A., A. P. Herbert, P. N. Barlow, V. M. Holers, and J. P. Hannan. 2008. Molecular basis of the interaction between complement receptor type 2 (CR2/CD21) and Epstein-Barr virus glycoprotein gp350. *J. Virol.* 82:11217-11227. doi:JVI.01673-081 [pii]; 10.1128/JVI.01673-08 [doi].
40. Yuan, X., M. J. Gubbins, and J. D. Berry. 2004. A simple and rapid protocol for the sequence determination of functional kappa light chain cDNAs from aberrant-chain positive murine hybridomas. *J. Immunol. Methods* 294:199-207.
41. Modrof J, Berting A, Tille B, Klotz A, Forstner C, Rieger S, Aberham C, Gessner M, Kreil T R. 2008. Neutralization of human parvovirus B19 by plasma and intravenous immunoglobulins. Transfusion 48:178-186.
42. Prins C, Gelfand E W, French L E. 2007. Intravenous immunoglobulin: properties, mode of action and practical use in dermatology. *Acta Derm Venereol* 87:206-218

What is claimed is:

1. A peptide of 40 amino acids or less comprising:

(i) a first domain comprising an amino acid sequence having at least 60% sequence identity with the sequence PDDRTLQ (SEQ ID NO: 1); and (ii) a second domain covalently linked to the first domain, said second domain comprising the amino acid sequence QNPVYLIPETVPYIKWDN (SEQ ID NO: 2);

wherein said peptide binds to monoclonal antibody clone 72A1.

2. The peptide of claim 1, wherein said first domain comprises an amino acid sequence having at least 70% sequence identity with the sequence PDDRTLQ (SEQ ID NO: 1).

3. The peptide of claim 1, wherein said first domain comprises the amino acid sequence PDDRTLQ (SEQ ID NO: 1) or DDRTLQ (SEQ ID NO: 3).

4. The peptide of claim 1, further comprising a linker between said first and second domains.

5. The peptide of claim 4, wherein said linker is an amino acid linker of 1 to 10 amino acids.

6. The peptide of claim 4, wherein said linker is an amino acid linker of 1 to 5 amino acids.

7. The peptide of claim 4, wherein said linker is an amino acid linker of 1 or 2 amino acids.

8. The peptide of claim 4, wherein said linker comprises one or more alanine and/or leucine residues.

9. The peptide of claim 1, wherein said peptide comprises the amino acid sequence DDRTLQLAQNPVYLI-PETVPYIKWDN (SEQ ID NO: 4).

10. A pharmaceutical composition comprising the peptide of claim 1 and a pharmaceutically acceptable carrier or excipient.

11. The pharmaceutical composition of claim 10, further comprising a vaccine adjuvant.

12. A method of (i) inducing the production of neutralizing antibodies against a gp350-expressing herpesvirus in an animal and/or (ii) immunizing or vaccinating an animal against a gp350-expressing herpesvirus, said method comprising administering an effective amount of the peptide of claim 1 to said animal.

13. The method of claim 12, wherein said gp350-expressing herpesvirus is Epstein-Barr virus (EBV).

14. The method of claim 12, wherein said animal is a human.

15. A method for detecting the presence or absence neutralizing antibodies against a gp350-expressing herpesvirus in a sample, the method comprising contacting the sample with the peptide of claim 1, and detecting the presence or absence of neutralizing antibodies/peptide complexes.

16. The method of claim 15, wherein sample is a biological sample from a subject infected with said gp350-expressing herpesvirus, or a subject who has been vaccinated or immunized against said gp350-expressing herpesvirus.

* * * * *

SEQUENCE LISTING

<160> NUMBER OF SEQ ID NOS: 41

<210> SEQ ID NO 1
<211> LENGTH: 7
<212> TYPE: PRT
<213> ORGANISM: Epstein-Barr virus

<400> SEQUENCE: 1

```
Pro Asp Asp Arg Thr Leu Gln
1               5
```

<210> SEQ ID NO 2
<211> LENGTH: 18
<212> TYPE: PRT
<213> ORGANISM: Epstein-Barr virus

<400> SEQUENCE: 2

```
Gln Asn Pro Val Tyr Leu Ile Pro Glu Thr Val Pro Tyr Ile Lys Trp
1               5                   10                  15

Asp Asn
```

<210> SEQ ID NO 3
<211> LENGTH: 6
<212> TYPE: PRT
<213> ORGANISM: Epstein-Barr virus

<400> SEQUENCE: 3

```
Asp Asp Arg Thr Leu Gln
1               5
```

<210> SEQ ID NO 4
<211> LENGTH: 26
<212> TYPE: PRT
<213> ORGANISM: Epstein-Barr virus

<400> SEQUENCE: 4

```
Asp Asp Arg Thr Leu Gln Leu Ala Gln Asn Pro Val Tyr Leu Ile Pro
1               5                   10                  15

Glu Thr Val Pro Tyr Ile Lys Trp Asp Asn
            20                  25
```

<210> SEQ ID NO 5
<211> LENGTH: 217
<212> TYPE: PRT
<213> ORGANISM: Mus musculus

<400> SEQUENCE: 5

```
Val Leu Ser Gln Leu Val Met Thr Gln Ser Pro Lys Ser Met Ser Met
1               5                   10                  15

Ser Val Gly Glu Arg Val Thr Leu Thr Cys Lys Ala Ser Glu Asn Val
            20                  25                  30

Val Thr Tyr Val Ser Trp Tyr Gln Gln Lys Pro Glu Gln Ser Pro Lys
        35                  40                  45

Leu Leu Ile Tyr Gly Ala Ser Asn Arg Tyr Thr Gly Val Pro Asp Arg
    50                  55                  60

Phe Thr Gly Ser Gly Ser Ala Thr Asp Phe Thr Leu Thr Ile Ser Ser
65                  70                  75                  80

Val Gln Ala Glu Asp Leu Ala Asp Tyr His Cys Gly Gln Gly Tyr Ser
                85                  90                  95

Tyr Pro Tyr Thr Phe Gly Gly Gly Thr Lys Leu Glu Ile Lys Arg Ala
            100                 105                 110
```

```
Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Ser Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215


<210> SEQ ID NO 6
<211> LENGTH: 450
<212> TYPE: PRT
<213> ORGANISM: Mus musculus

<400> SEQUENCE: 6

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Leu His Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Trp Gly Asn Tyr Pro His Tyr Ala Met Asp Tyr Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
```

```
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 7
<211> LENGTH: 303
<212> TYPE: PRT
<213> ORGANISM: Epstein-Barr virus

<400> SEQUENCE: 7

Ala Leu Leu Val Cys Gln Tyr Thr Ile Gln Ser Leu Ile Gln Leu Thr
1               5                   10                  15

Arg Asp Asp Pro Gly Phe Phe Asn Val Glu Ile Leu Glu Phe Pro Phe
            20                  25                  30

Tyr Pro Ala Cys Asn Val Cys Thr Ala Asp Val Asn Ala Thr Ile Asn
        35                  40                  45

Phe Asp Val Gly Gly Lys Lys His Lys Leu Asn Leu Asp Phe Gly Leu
    50                  55                  60

Leu Thr Pro His Thr Lys Ala Val Tyr Gln Pro Arg Gly Ala Phe Gly
65                  70                  75                  80

Gly Ser Glu Asn Ala Thr Asn Leu Phe Leu Leu Glu Leu Leu Gly Ala
                85                  90                  95

Gly Glu Leu Ala Leu Thr Met Arg Ser Lys Lys Leu Pro Ile Asn Ile
            100                 105                 110

Thr Ala Gly Glu Glu Gln Gln Val Ser Leu Glu Ser Val Asp Val Tyr
        115                 120                 125

Phe Gln Asp Val Phe Gly Thr Met Trp Cys His His Ala Glu Met Gln
    130                 135                 140

Asn Pro Val Tyr Leu Ile Pro Glu Thr Val Pro Tyr Ile Lys Trp Asp
145                 150                 155                 160

Asn Cys Asn Ser Thr Asn Ile Thr Ala Val Val Arg Ala Gln Gly Leu
                165                 170                 175
```

```
Asp Val Thr Leu Pro Leu Ser Leu Pro Thr Ser Ala Gln Asp Ser Asn
            180                 185                 190

Phe Ser Val Lys Thr Glu Met Leu Gly Asn Glu Ile Asp Ile Glu Cys
        195                 200                 205

Ile Met Glu Asp Gly Glu Ile Ser Gln Val Leu Pro Gly Asp Asn Lys
    210                 215                 220

Phe Asn Ile Thr Cys Ser Gly Tyr Glu Ser His Val Pro Ser Gly Gly
225                 230                 235                 240

Ile Leu Thr Ser Thr Ser Pro Val Ala Thr Pro Ile Pro Gly Thr Gly
                245                 250                 255

Tyr Ala Tyr Ser Leu Arg Leu Thr Pro Arg Pro Val Ser Arg Phe Leu
            260                 265                 270

Gly Asn Asn Ser Ile Leu Tyr Val Phe Tyr Ser Gly Asn Gly Pro Lys
        275                 280                 285

Ala Ser Gly Gly Asp Tyr Cys Ile Gln Ser Asn Ile Val Phe Ser
    290                 295                 300


<210> SEQ ID NO 8
<211> LENGTH: 886
<212> TYPE: PRT
<213> ORGANISM: Epstein-Barr virus

<400> SEQUENCE: 8

Met Glu Ala Ala Leu Leu Val Cys Gln Tyr Thr Ile Gln Ser Leu Ile
1               5                   10                  15

Gln Leu Thr Arg Asp Asp Pro Gly Phe Phe Asn Val Glu Ile Leu Glu
            20                  25                  30

Phe Pro Phe Tyr Pro Ala Cys Asn Val Cys Thr Ala Asp Val Asn Ala
        35                  40                  45

Thr Ile Asn Phe Asp Val Gly Gly Lys Lys His Lys Leu Asn Leu Asp
    50                  55                  60

Phe Gly Leu Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Ile Thr Thr Gly Glu Glu Gln Gln Val Ser Leu Glu Ser Val
        115                 120                 125

Asp Val Tyr Phe Gln Asp Val Phe Gly Thr Met Trp Cys His His Ala
    130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205

Ile Glu Cys Ile Met Glu Asp Gly Glu Ile Ser Gln Val Leu Pro Gly
    210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255
```

-continued

```
Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
    290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
    370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Leu Asn Thr Thr Gly Phe Ala Ala Pro Asn Thr Thr Thr Gly Leu
        435                 440                 445

Pro Ser Ser Thr His Val Pro Thr Asn Leu Thr Ala Pro Ala Ser Thr
    450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Arg Asp
                485                 490                 495

Asn Gly Thr Glu Ser Lys Ala Pro Asp Met Thr Ser Pro Thr Ser Ala
            500                 505                 510

Val Thr Thr Pro Thr Pro Asn Ala Thr Ser Pro Thr Pro Ala Val Thr
        515                 520                 525

Thr Pro Thr Pro Asn Ala Thr Ser Pro Thr Leu Gly Lys Thr Ser Pro
    530                 535                 540

Thr Ser Ala Val Thr Thr Pro Thr Pro Asn Ala Thr Ser Pro Thr Pro
545                 550                 555                 560

Ala Val Thr Thr Pro Thr Pro Asn Ala Thr Ile Pro Thr Leu Gly Lys
                565                 570                 575

Thr Ser Pro Thr Ser Ala Val Thr Thr Pro Thr Pro Asn Ala Thr Ser
            580                 585                 590

Pro Thr Val Gly Glu Thr Ser Pro Gln Ala Asn Thr Thr Asn His Thr
        595                 600                 605

Leu Gly Gly Thr Ser Ser Thr Pro Val Val Thr Ser Pro Pro Lys Asn
    610                 615                 620

Ala Thr Ser Ala Val Thr Thr Gly Gln His Asn Ile Thr Ser Ser Ser
625                 630                 635                 640

Thr Ser Ser Met Ser Leu Arg Pro Ser Ser Ile Ser Glu Thr Leu Ser
                645                 650                 655

Pro Ser Thr Ser Asp Asn Ser Thr Ser His Met Pro Leu Leu Thr Ser
            660                 665                 670
```

```
Ala His Pro Thr Gly Gly Glu Asn Ile Thr Gln Val Thr Pro Ala Ser
        675                 680                 685

Thr Ser Thr His His Val Ser Thr Ser Ser Pro Ala Pro Arg Pro Gly
    690                 695                 700

Thr Thr Ser Gln Ala Ser Gly Pro Gly Asn Ser Ser Thr Ser Thr Lys
705                 710                 715                 720

Pro Gly Glu Val Asn Val Thr Lys Gly Thr Pro Pro Lys Asn Ala Thr
                725                 730                 735

Ser Pro Gln Ala Pro Ser Gly Gln Lys Thr Ala Val Pro Thr Val Thr
            740                 745                 750

Ser Thr Gly Gly Lys Ala Asn Ser Thr Thr Gly Gly Lys His Thr Thr
        755                 760                 765

Gly His Gly Ala Arg Thr Ser Thr Glu Pro Thr Thr Asp Tyr Gly Gly
    770                 775                 780

Asp Ser Thr Thr Pro Arg Thr Arg Tyr Asn Ala Thr Thr Tyr Leu Pro
785                 790                 795                 800

Pro Ser Thr Ser Ser Lys Leu Arg Pro Arg Trp Thr Phe Thr Ser Pro
                805                 810                 815

Pro Val Thr Thr Ala Gln Ala Thr Val Pro Val Pro Pro Thr Ser Gln
            820                 825                 830

Pro Arg Phe Ser Asn Leu Ser Met Leu Val Leu Gln Trp Ala Ser Leu
        835                 840                 845

Ala Val Leu Thr Leu Leu Leu Leu Leu Val Met Ala Asp Cys Ala Phe
    850                 855                 860

Arg Arg Asn Leu Ser Thr Ser His Thr Tyr Thr Thr Pro Pro Tyr Asp
865                 870                 875                 880

Asp Ala Glu Thr Tyr Val
                885


<210> SEQ ID NO 9
<211> LENGTH: 658
<212> TYPE: PRT
<213> ORGANISM: Epstein-Barr virus

<400> SEQUENCE: 9

Met Glu Ala Ala Leu Leu Val Cys Gln Tyr Thr Ile Gln Ser Leu Ile
1               5                   10                  15

Gln Leu Thr Arg Asp Asp Pro Gly Phe Phe Asn Val Glu Ile Leu Glu
            20                  25                  30

Phe Pro Phe Tyr Pro Ala Cys Asn Val Cys Thr Ala Asp Val Asn Ala
        35                  40                  45

Thr Ile Asn Phe Asp Val Gly Gly Lys Lys His Lys Leu Asn Leu Asp
    50                  55                  60

Phe Gly Leu Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Ile Thr Thr Gly Glu Glu Gln Gln Val Ser Leu Glu Ser Val
        115                 120                 125

Asp Val Tyr Phe Gln Asp Val Phe Gly Thr Met Trp Cys His His Ala
    130                 135                 140

Glu Met Gln Asn Pro Val Tyr Leu Ile Pro Glu Thr Val Pro Tyr Ile
145                 150                 155                 160
```

-continued

```
Lys Trp Asp Asn Cys Asn Ser Thr Asn Ile Thr Ala Val Val Arg Ala
                165                 170                 175

Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
        195                 200                 205

Ile Glu Cys Ile Met Glu Asp Gly Glu Ile Ser Gln Val Leu Pro Gly
    210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
                245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
        275                 280                 285

Gly Pro Lys Ala Ser Gly Gly Asp Tyr Cys Ile Gln Ser Asn Ile Val
    290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
                325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
        355                 360                 365

Thr Ser Gly Thr Pro Ser Gly Cys Glu Asn Ile Ser Gly Ala Phe Ala
    370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
                405                 410                 415

His Lys Val Ile Phe Ser Lys Ala Pro Glu Ser Thr Thr Thr Ser Pro
            420                 425                 430

Thr Leu Asn Thr Thr Gly Phe Ala Ala Pro Asn Thr Thr Thr Gly Leu
        435                 440                 445

Pro Ser Ser Thr His Val Pro Thr Asn Leu Thr Ala Pro Ala Ser Thr
    450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Arg Asp
                485                 490                 495

Asn Gly Thr Glu Ser Thr Pro Pro Lys Asn Ala Thr Ser Pro Gln Ala
            500                 505                 510

Pro Ser Gly Gln Lys Thr Ala Val Pro Thr Val Thr Ser Thr Gly Gly
        515                 520                 525

Lys Ala Asn Ser Thr Thr Gly Gly Lys His Thr Thr Gly His Gly Ala
    530                 535                 540

Arg Thr Ser Thr Glu Pro Thr Thr Asp Tyr Gly Gly Asp Ser Thr Thr
545                 550                 555                 560

Pro Arg Thr Arg Tyr Asn Ala Thr Thr Tyr Leu Pro Pro Ser Thr Ser
                565                 570                 575
```

```
Ser Lys Leu Arg Pro Arg Trp Thr Phe Thr Ser Pro Pro Val Thr Thr
            580                 585                 590

Ala Gln Ala Thr Val Pro Val Pro Pro Thr Ser Gln Pro Arg Phe Ser
        595                 600                 605

Asn Leu Ser Met Leu Val Leu Gln Trp Ala Ser Leu Ala Val Leu Thr
    610                 615                 620

Leu Leu Leu Leu Leu Val Met Ala Asp Cys Ala Phe Arg Arg Asn Leu
625                 630                 635                 640

Ser Thr Ser His Thr Tyr Thr Thr Pro Pro Tyr Asp Asp Ala Glu Thr
                645                 650                 655

Tyr Val


<210> SEQ ID NO 10
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 10

ctgaggagac ggtgaccatg gtcccttggc ccc                                    33


<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 11

cgtttgattt ccagcttggt ccc                                               23


<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12

acctattact gtcagcacat ta                                                22


<210> SEQ ID NO 13
<211> LENGTH: 14
<212> TYPE: PRT
<213> ORGANISM: Homo sapiens

<400> SEQUENCE: 13

Trp Gly Gln Gly Thr Met Val Thr Val Ser Ser Ala Ser Thr
1               5                   10


<210> SEQ ID NO 14
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 14

tggggccaag ggacaatggt caccgtctct tcagcctcca cc                          42


<210> SEQ ID NO 15
<211> LENGTH: 22
```

<212> TYPE: DNA
<213> ORGANISM: Artificial Sequence
<220> FEATURE:
<223> OTHER INFORMATION: Synthetic oligonucleotide

<400> SEQUENCE: 15
tcatttaccc ggagacaggg ag 22

<210> SEQ ID NO 16
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 16
gggaccaagc tggaaatcaa acg 23

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
ctccctctaa cactctcccc tg 22

<210> SEQ ID NO 18
<211> LENGTH: 18
<212> TYPE: PRT
<213> ORGANISM: Epstein-Barr virus

<400> SEQUENCE: 18

Ser Val Lys Thr Glu Met Leu Gly Asn Glu Ile Asp Ile Glu Cys Ile
1 5 10 15

Met Glu

<210> SEQ ID NO 19
<211> LENGTH: 4
<212> TYPE: PRT
<213> ORGANISM: Epstein-Barr virus

<400> SEQUENCE: 19

Lys Ala Ser Gly
1

<210> SEQ ID NO 20
<211> LENGTH: 11
<212> TYPE: PRT
<213> ORGANISM: Mus musculus

<400> SEQUENCE: 20

Lys Ala Ser Glu Asn Val Val Thr Tyr Val Ser
1 5 10

<210> SEQ ID NO 21
<211> LENGTH: 7
<212> TYPE: PRT
<213> ORGANISM: Mus musculus

<400> SEQUENCE: 21

Gly Ala Ser Asn Arg Tyr Thr
1 5

<210> SEQ ID NO 22
<211> LENGTH: 9
<212> TYPE: PRT
<213> ORGANISM: Mus musculus

<400> SEQUENCE: 22

Gly Gln Gly Tyr Ser Tyr Pro Tyr Thr
1 5

<210> SEQ ID NO 23
<211> LENGTH: 9
<212> TYPE: PRT
<213> ORGANISM: Mus musculus

<400> SEQUENCE: 23

Phe Thr Phe Ser Ser Phe Gly Met His
1 5

<210> SEQ ID NO 24
<211> LENGTH: 18
<212> TYPE: PRT
<213> ORGANISM: Mus musculus

<400> SEQUENCE: 24

Ile Ser Ser Gly Ser Ser Thr Leu His Tyr Ala Asp Thr Val Lys Gly
1 5 10 15

Arg Phe

<210> SEQ ID NO 25
<211> LENGTH: 11
<212> TYPE: PRT
<213> ORGANISM: Mus musculus

<400> SEQUENCE: 25

Trp Gly Asn Tyr Pro His Tyr Ala Met Asp Tyr
1 5 10

<210> SEQ ID NO 26
<211> LENGTH: 5
<212> TYPE: PRT
<213> ORGANISM: Mus musculus

<400> SEQUENCE: 26

Gln Leu Val Met Thr
1 5

<210> SEQ ID NO 27
<211> LENGTH: 24
<212> TYPE: PRT
<213> ORGANISM: Epstein-Barr virus

<400> SEQUENCE: 27

Gly Ser Ala Lys Pro Gly Asn Gly Ser Tyr Phe Ala Ser Val Lys Thr
1 5 10 15

Glu Met Leu Gly Asn Glu Ile Asp
20

<210> SEQ ID NO 28
<211> LENGTH: 11
<212> TYPE: PRT
<213> ORGANISM: Epstein-Barr virus

<400> SEQUENCE: 28

-continued

Phe Tyr Ser Gly Asn Gly Pro Lys Ala Ser Gly
1 5 10

<210> SEQ ID NO 29
<211> LENGTH: 12
<212> TYPE: PRT
<213> ORGANISM: Epstein-Barr virus

<400> SEQUENCE: 29

Ser Val Lys Thr Glu Met Leu Gly Asn Glu Ile Asp
1 5 10

<210> SEQ ID NO 30
<211> LENGTH: 7
<212> TYPE: PRT
<213> ORGANISM: Epstein-Barr virus

<400> SEQUENCE: 30

Gln Leu Thr Arg Asp Asp Pro
1 5

<210> SEQ ID NO 31
<211> LENGTH: 21
<212> TYPE: PRT
<213> ORGANISM: Epstein-Barr virus

<400> SEQUENCE: 31

Ser Lys Ala Pro Glu Ser Thr Thr Thr Ser Pro Thr Leu Asn Thr Thr
1 5 10 15

Gly Phe Ala Asp Tyr
20

<210> SEQ ID NO 32
<211> LENGTH: 26
<212> TYPE: PRT
<213> ORGANISM: Epstein-Barr virus

<400> SEQUENCE: 32

Glu Glu Lys Ser Ala Glu Ala Ala Gln Gln Pro Ala Asp Ala Ala Pro
1 5 10 15

Asp Ser Ala Pro Asp Ala Lys Met Asp Gln
20 25

<210> SEQ ID NO 33
<211> LENGTH: 26
<212> TYPE: PRT
<213> ORGANISM: Epstein-Barr virus

<400> SEQUENCE: 33

Ala Ala Ala Ala Ala Ala Ala Ala Gln Asn Pro Val Tyr Leu Ile Pro
1 5 10 15

Glu Thr Val Pro Tyr Ile Lys Trp Asp Asn
20 25

<210> SEQ ID NO 34
<211> LENGTH: 27
<212> TYPE: PRT
<213> ORGANISM: Epstein-Barr virus

<400> SEQUENCE: 34

Asp Asp Arg Thr Leu Gln Leu Ala Ala Ala Pro Val Ala Ala Leu Ile
1 5 10 15

Pro Ala Val Val Pro Ala Ile Ala Trp Ala Ala 20 25

<210> SEQ ID NO 35
<211> LENGTH: 7
<212> TYPE: PRT
<213> ORGANISM: Homo sapiens

<400> SEQUENCE: 35

Gly Thr Lys Leu Glu Ile Lys
1 5

<210> SEQ ID NO 36
<211> LENGTH: 8
<212> TYPE: PRT
<213> ORGANISM: Mus musculus

<400> SEQUENCE: 36

Gly Ser Ser Phe Thr Asp Tyr Thr
1 5

<210> SEQ ID NO 37
<211> LENGTH: 8
<212> TYPE: PRT
<213> ORGANISM: Mus musculus

<400> SEQUENCE: 37

Ile Asn Pro Tyr Asn Gly Gly Thr
1 5

<210> SEQ ID NO 38
<211> LENGTH: 12
<212> TYPE: PRT
<213> ORGANISM: Mus musculus

<400> SEQUENCE: 38

Ala Gly Gly Leu Arg Arg Val Asn Trp Phe Ala Tyr
1 5 10

<210> SEQ ID NO 39
<211> LENGTH: 9
<212> TYPE: PRT
<213> ORGANISM: Mus musculus

<400> SEQUENCE: 39

Thr Gly Ala Val Thr Thr Ser Asn Tyr
1 5

<210> SEQ ID NO 40
<211> LENGTH: 9
<212> TYPE: PRT
<213> ORGANISM: Mus musculus

<400> SEQUENCE: 40

Val Leu Trp His Ser Asn His Trp Val
1 5

<210> SEQ ID NO 41
<211> LENGTH: 11
<212> TYPE: PRT
<213> ORGANISM: Epstein-Barr virus

<400> SEQUENCE: 41

Gly Ser Ala Lys Pro Gly Asn Gly Ser Tyr Phe
1 5 10